(12) United States Patent
Simpkins et al.

(10) Patent No.: US 6,319,914 B1
(45) Date of Patent: *Nov. 20, 2001

(54) CYTOPROTECTIVE EFFECT OF POLYCYCLIC PHENOLIC COMPOUNDS

(75) Inventors: James W. Simpkins, Gainesville, FL (US); Katherine D. Gordon, Winchester, MA (US); Pattie S. Green, Gainesville, FL (US)

(73) Assignees: Apollo BioPharmaceuticals, Inc., Cambridge, MA (US); University of Florida Research Foundation, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/351,492

(22) Filed: Jul. 12, 1999

Related U.S. Application Data

(60) Continuation-in-part of application No. 09/129,209, filed on Aug. 4, 1998, now Pat. No. 6,197,833, which is a division of application No. 08/685,574, filed on Jul. 24, 1996, now Pat. No. 5,859,001, and a division of application No. 09/128,862, filed on Aug. 4, 1998, which is a division of application No. 08/782,883, filed on Jan. 10, 1997, now Pat. No. 5,874,672, and a division of application No. 09/179,640, filed on Oct. 27, 1998, which is a division of application No. 08/749,703, filed on Nov. 15, 1996, now Pat. No. 5,877,169, which is a continuation-in-part of application No. 08/685,574, filed on Jul. 24, 1996, now Pat. No. 5,859,001, and a continuation-in-part of application No. 08/648,857, filed on May 16, 1996, now Pat. No. 5,843,934, which is a division of application No. 08/318,042, filed on Oct. 4, 1994, now Pat. No. 5,554,601, which is a continuation-in-part of application No. 08/149,175, filed on Nov. 5, 1993, now abandoned.

(51) Int. Cl.$^7$ .................... A61K 36/00; A61K 31/05
(52) U.S. Cl. ............ 514/182; 514/179; 514/180; 514/181; 514/903; 514/732
(58) Field of Search ................ 514/179, 180, 514/181, 182, 903, 732

(56) References Cited

U.S. PATENT DOCUMENTS

| | | | |
|---|---|---|---|
| 4,897,389 | 1/1990 | Aroonsakal | 514/171 |
| 4,957,909 | 9/1990 | Abou-Gharbia et al. | 514/75 |
| 5,002,965 | 3/1991 | Ramwell et al. | |
| 5,051,352 | 9/1991 | Martindale et al. | |
| 5,109,017 | 4/1992 | Schmiesing et al. | 514/438 |
| 5,393,763 | 2/1995 | Black | 514/333 |
| 5,457,117 | 10/1995 | Black | 514/337 |
| 5,510,370 | 4/1996 | Hock | 514/443 |
| 5,512,557 | 4/1996 | Collins | 514/182 |
| 5,550,029 | 8/1996 | Simpkins et al. | 435/14 |
| 5,554,601 | * 9/1996 | Simpkins et al. | 514/182 |
| 5,641,790 | 6/1997 | Draper | 514/333 |
| 5,646,137 | 7/1997 | Black et al. | 514/171 |
| 5,733,926 | 3/1998 | Gorbach | 514/456 |
| 5,824,672 | * 10/1998 | Simpkins et al. | 514/182 |
| 5,843,934 | 12/1998 | Simpkins | 514/182 |
| 5,859,001 | 1/1999 | Simpkins et al. | 514/182 |
| 5,877,169 | * 3/1999 | Simpkins | 514/179 |
| 5,914,325 | 6/1999 | Droescher et al. | 514/182 |
| 5,952,374 | 9/1999 | Clarkson et al. | 514/456 |
| 5,972,923 | 10/1999 | Simpkins et al. | 514/182 |
| 5,977,096 | 11/1999 | Droescher et al. | 514/178 |
| 6,172,056 | 1/2001 | Droescher et al. | 514/182 |

FOREIGN PATENT DOCUMENTS

| | | |
|---|---|---|
| 339 579 | 11/1989 | (EP) . |
| 0 606 661 | 7/1994 | (EP) . |
| 0659418 A1 | * 6/1995 | (EP) . |
| 0 659 418 | 6/1995 | (EP) . |
| 92/03049 | * 3/1992 | (WO) . |
| WO92/03049 | 3/1992 | (WO) . |
| WO92/07855 | 5/1992 | (WO) . |
| 92/07855 | * 5/1992 | (WO) . |
| WO92/13538 | 8/1992 | (WO) . |
| WO 95/13076 | 11/1993 | (WO) . |
| WO95/10513 | 4/1995 | (WO) . |
| WO 98/43647 | 10/1998 | (WO) . |

OTHER PUBLICATIONS

Behl et al., Biochem. Biophys. Res. Commun., 216(2), 1995, 473–82.*

HCAPLUS DN 126:70328, Green et al., Neurosci. Lett., 218(3), 1996, 165–168 (abstract).*

Huggins, Charles, et al., Chemical Structure of Steroids in relation to promotion of growth of the vagina and uterus of the hypophy sectorized rat; Journal of Experimental Medicine, vol. 100, pp. 225–243, (1954).

Nomenclature of Inorganic Chemistry: J. American Chemical Society, vol. 82, pp. 5525–5581, (1960).

Black, L. et al., Factors Affecting the Dye Exclusion Test for Cell Viability, 35:9–13 (1964).

Korenman, Stanley G., Comparative Binding Affinity of Estrogens and its Relation to Estrogenic Potency, vol. 13, pp. 163–177 (1969).

Definitive Rules for Nomenclature of Steroids: Pure and Applied Chemistry, vol. 31, pp. 285–322 (1972).

Chernayaev, G.A., et al., A Series of Optical, Structural and Isomeric Analogs of Estradiol: A Comparative Study of the Biological Activity and Affinity to Cytosol Receptor of Rabbit Uterus, The Journal of Steroid Biochemistry, vol. 6, pp 1483–1488. (1975).

Hackman, B. W., et al., "Replacement Therapy with Piperazine Oestrone Sulphate ('Harmogen') and Its Effect on Memory," Current Medical Research and Opinion 4:303–306 (1976).

(List continued on next page.)

Primary Examiner—Dwayne C. Jones
Assistant Examiner—C. Delacroix-Muirheid
(74) Attorney, Agent, or Firm—Bromberg & Sunstein LLP

(57) ABSTRACT

The invention comprises methods for conferring a cytoprotective effect on a population of cells, such as providing a polycyclic phenolic compound in a physiologically acceptable formulation, and administering the formulation in an effective dose to the population of cells.

36 Claims, 15 Drawing Sheets

OTHER PUBLICATIONS

Perez–Polo, J. R., et al., Steroid Induction of Nerve Growth Factor Synthesis in Cell Culture; Life Sci. 21, pp. 1535–1543 (1976).

Utian, Wulf, Current Status of Menopause and Postmenopausal Estrogen Therapy; Obstetrical and Gynecological Survey, vol. 32, No. 4, pp. 193–197 (1976).

Pons, Michael, et al., Structural Requirements for Maximal Inhibitory Allosteric Effect of Estrogens and Estrogen Analogues on Glutamate Dehydrogenase, Eur. J. Biochemistry, vol. 84, pp. 257–266, (1978).

Beatty William., Gonadal Hormones and Sex Differences in Nonreproductive Behavior in Rodents: Organizational and Activational Influences; Hormones and Behavior, vol. 12, pp. 112–163 (1979).

Loy, Rebekah et al., Sexual Dimorphism in Extent of Axonal Sprouting in Rat Hippocampus, Science vol. 208, pp. 1282–1284 (1980).

Matsumoto, Akira et al., "Neuronal Plasticity in the Deafferented Hypothalamic Arcuate Nucleus of Adult Female Rats and Its Enhancement by Treatment with Estrogen," The Journal of Comparative Neurology, vol. 197, pp. 197–205 (1981).

Nishizuka, M., et al., "Oranizational action of estrogen on synaptic pattern in the amygdala: implications for sexual differentiation of the brain"; Brain Research vol. 213, pp. 422–426 (1981).

Toran–Allerand, C. Dominique, "Gonadal Steroids and Brain Development—In Vitro Veritas?", TINS, pp. 118–121 (May 1981).

Arvidson, Nils Gunnar, et al., "Oestrogens and anti–oestrogens show dissociation between early uterine vasular responses and uterotrophic effects in mice", Acta Endocrinologica, vol. 100, pp. 290–294 (1982).

Barde, Yves–Alain, et al., "Purification of a neurotrophic factor from mammalian brain", EMBO J., vol. 1, pp. 549–553 (1982).

Clark, James H., et al., "Effects of Estradol–17x on Nuclear Occupancy of the Estrogen Receptor, Stimulation of Nuclear Type II Sites and Uterine Growth", Journal of Steroid Biochemistry, vol. 16, pp. 323–328 (1982).

Hier, Daniel B., et al., "Spatial Ability in Androgen–Deficient Men," The New England Journal of Medicine, vol. 306, pp. 1202–1205 (1982).

Clark, James H., et al, "The Agonistic and Antagonistic Effects of Short Acting Estrogens: A Review", Pharmacy Ther., vol. 21, pp. 429–453 (1983).

Toran–Allerand, C. Dominique, et al., "Sex Steroids and the Development of the Newborn Mouse Hypothalamus and Preoptic Area in Vitro: III. Effects of Estrogen on Dendritic Differentiation," Developmental Brain Research vol. 7, pp. 97–101 (1983).

Namba, H., et al., "Acute administration of high doses of estrogen increases glucose utilization throughout brain", Brain Research, vol. 291, pp. 391–394 (1984).

Collins, Aila, et al., "Psychoneuroendocrine Stress Responses and Mood as Related to the Menstrual Cycle," Psychosomatic Medicine, vol. 47, pp. 512–527 (1985).

Gabrieli, J. D. E., et al., "The Influence of Sex Steroids on Human Nonverbal Memory Processes," Ann. NY Academy of Sciences, vol. 444, pp. 457–459 (1985).

Papendorp, John T., "On the role of 17 Alpha–Estradiol and 17 Beta–Estradiol in the Proliferation of MCF7 and T47D–A11 Human Breast Tumor Cells" Journal of Cellular Physiology, vol. 125, pp. 591–595 (1985).

Aizenman, Yair, et al., "Changes in insulin and transferrin requirements of pure brain neuronal cultures during embryonic development" Proc. Nat'l. Acad. Sci. U.S.A., vol. 83, pp. 2263–2266 (1986).

Arimatsu, Yasuyoshi, et al., "Estrogen Treatment Enchances Survival of Cultured Fetal Rat Amygdala neurons in a Defined Medium" Developmental Brain Research, vol. 26 pp. 151–159 (1986).

Fillit, Howard, et al., "Observations in a Preliminary Open Trial of Estradiol Therapy for Senile Dementia–Alzheimer's Type," Psychoneuroendocrinology, vol. 11, pp. 337–345 (1986).

Morrison, Richard S., et al., "Basic fibroblast growth factor supports the survival of cerebral cortical neurons in primary culture", Proc. Natl. Acad. Sci. U.S.A., vol. 83, pp. 7537–7541 (1986).

Morse, Joanne K., et al., "Gonadal Steroids Influence Axon Sprouting in the Hippocampal Dentate Gyrus: A Sexually Dimorphic Response," Experimental Neurology, vol. 94, pp. 649–658 (1986).

Braughler, J. Mark, et al, "Novel 21–Amino Steroids as Potent Inhibitors of Iron–dependent Lipid Peroxidation", The Journal of Biological Chemistry, vol. 262, No. 22, pp. 10438–10440 (1987).

Wright, L. L., et al., "The Role of Neuron Death in the Development of the Gender Difference in the Number of Neurons in the Rat Superior Cervical Ganglion", Int. J. Dev. Neurosci., vol. 5, No. 4, pp. 305–311 (1987).

Morrison, Richard S., et al., "Trophic Stimulation of Cultured Neurons from Neonatal Rat Brain by Epidermal Growth Factor", Science, vol. 238, pp. 72–75 (1987).

Nakano, Minoru, et al, "Novel and Potent Biological Antioxidants on Membrane Phospholipid Peroxidation: 2–Hydroxy Estrone and 2–Hydroxy Estradiol", Biochemical and Biophysical Research Communication, vol. 142, No. 3, pp. 919–924 (1987).

Niki, Etsuo, "Antioxidants in Relation to Lipid Peroxidation" Chemistry and Physics of Lipids, vol. 44, p. 227–253 (1987).

Sugioka, Katsauki, et al, "Estrogens as natural antioxidants of membrane phospholipid peroxidation", Federation of European Biochemical Societies, vol. 210, No. 1, pp. 37–39 (1987).

Thoenen, Hans, et al., "The Physiological Function of Nerve Growth Factor in the Central Nervous System: Comparison with the Periphery", Rev. Physiol. Biochem. Pharmacol., vol. 109, pp. 145–178 (1987).

Jones, Kathryn J., "Steroid Hormones and Neurotrophism: Relationship to Nerve Injury," Metabolic Brain Disease, vol. 3, No. 1, pp. 1–18 (1988).

Mouton, Peter R., et al., "Induction of cortical cholinergic hypofunction and memory retention deficits through intracortical AF64A infusions", Brain Research, Vol. 444, pp. 104–118 (1988).

Paganini–Hill, Annlia, et al., "Postmenopausal oestrogen treatment and stroke: a prospective study", Brit. Med. Journal., vol. 297, 519–522, (1988).

Scheff, et al., "Neurotrophic Effects of Steroids on Lesion–Induced Growth in the Hippocampus. I. The Asteroidal Condition," Brain Research, vol. 457, pp. 246–250 (1988).

Sherwin, Barbara B., "Affective Changes with Estrogen and Androgen Replacement Therapy in Surgically Menopausal Women," Journal of Affective Disorders, vol. 14 pp. 177–187 (1988).

Simpkins, James W., et al., "A Brain– Enhanced Chemical Delivery System for Gonadal Steroids: Implications for Neurodegenerative Diseases", Adv. Behav. Biol., vol. 36, pp. 197–212 (1989).

Diaz–Veliz, Gabriela, et al., "Influence of the Estrous Cycle, Ovariectomy and Estradiol Replacement Upon the Acquisition of Conditioned Avoidance Responses in Rats," Physiology & Behavior, vol. 46, pp. 397–401 (1989).

Garcia–Segura, L. M., et al., "Estradiol Induces Rapid Remodeling of Plasma Membranes in Developing Rat Cerebrocortical Neurons in Culture," Brain Research, vol. 498, pp. 339–343 (1989).

Hefti, F., et al., "Function of Neurotrophic Factors in the Adult and Aging Brain and Their Possible Use in the Treatment of Neurodegenerative Diseases", Neurobiol. Aging, vol. 10, pp. 515–533 (1989).

Honjo, Hideo, et al., "In Vivo Effects by Estrone Sulfate on the Central Nervous System–Senile Dementia (Alzheimer's Type)", Steroid Biochemistry, vol. 34, pp. 521–524 (1989).

Dimlich, R. V. W., et al, "Effects of a 21–Aminosteroid (U–74006F) on Cerebral Metabolites and Edema After Severe Experimental Head Trauma", Advances in Neurology, vol. 52, pp. 365–375 (1990).

Ernfors, Patrick, et al., "Identification of Cells in Rat Brain and Peripheral Tissues Expressing mRNA for Members of the Nerve Growth Factor Family", Neuron, vol. 5 pp. 511–526 (1990).

Jacobsen, E. Jon, et al, "Novel 21–Aminosteroid that Inhibit Iron–Dependent Lipid Peroxidation and Protect Against Central Nervous System Trauma", Journal Medical Chemistry, vol. 33, pp. 1145–1151 (1990).

Katoh–Semba, Ritsuko, et al., "Influences of Neonatal and Adult Exposures to Testosterone on the Levels of the $\beta\beta$–subunit of Nerve Growth Factor in the Neural Tissues of Mice," Brain Research, vol. 522, pp. 112–117 (1990).

Komuro, Erika, et al., "Inhibition of Peroxidations of Lipids and Membranes by Estrogens", Journal of Physical Organic Chemistry, vol. 3, pp. 309–315 (1990).

Kovesdi, Imre, et al., "Heparin–Binding Neurotrophic Factor (HBNF) and MK, Members of a New Family of Homologous, Developmentally Regulated Proteins", Biochemical and Biophysical Research Communications, vol. 172, pp. 850–854 (1990).

Monyer, Hannelore, et al., "21–Aminosteroids Attenuate Excitotoxic Neuronal Injury in Cortical Cell Cultures," Neuron, vol. 5, pp. 121–126 (1990).

Sherwin, Barbara, et al., "Estrogen and Cognitive Functioning in Surgically Menopausal Women," Annals NY Acad. Sci. vol. 592, pp. 474–475 (1990).

Sherwin, Barbara, et al., "Up–Regulatory Effect of Estrogen on Platelet 3H–Imipramine Binding Sites in Surgically Menopausal Women," Biol. Psychiatry, vol. 28 pp. 339–348 (1990).

Woolley, Catherine S., et al., "Naturally Occurring Fluctuation in Dendritic Spine Density on Adult Hippocampal Pyramidal Neurons," Journal of Neuroscience, vol. 10, pp. 4035–4039 (1990).

Cheng, Leland P., et al., "Inhibition of Myointimal Hyperplasia and Macrophage Infiltration by Estradiol in Aorta Allografts", Transplantation, vol. 52, No. 6, pp. 967–972 (1991).

Garris, Paul A., et al., "Estradiol Rapidly Stimulates Dopamine Release from the Posterior Pituitary in Vitro", Neuroendrocinology, vol. 53, pp. 601–607 (1991).

Hall, Edward, et al. "Sex Differences in Postischemic Neuronal Necrosis in Gerbils" Journal of Cerebral Blood Flow Metabolism, vol. 11, p. 292 (1991).

Behl, Christian, et al, "Vitamin E Protects Nerve Cells from Amyloid B Protein Toxicity", Biochemical and Biophysical Research Communications, vol. 186, No. 2, pp. 944–950 (1992).

Hall, Ph.D., "The neuroprotective pharmacology of methylprednisolone", Journal of Neurosurgery., vol. 76, pp. 13–22 (1992).

Hirasawa, K., et al, "Female Sex Hormone, Estradiol, Antagonizes the Immunosuppressive Activity of Cyclosporine in Rat Organ Transplantation", Transplantation Proceedings, vol. 24, No. 1, pp. 408–409 (1992).

Honjo et al., "Estrogen as a Growth Factor to Central Nervous Cells", Journal of Steroid Biochem. Molec. Biol., vol. 41, pp. 633–635 (1992).

Kostanyan et al., "Rat brain glycolysis regulation by estradiol–17 B", Biochem. Biophys. Acta, vol. 1133, pp. 301–306 (1992).

Gomez–Mancilla, et al., "Effect of Estrogen and Progesterone on L–DOPA induced dyskinesia in MPTP–treated monkeys", Neuroscience Letters, vol. 135, pp. 129–132 (1992).

Hatton, et al., "Effects of Ovariectomy and Estrogen Replacement on Dye Coupling Among Rat Supraoptic Nucleus Neurons"., Brain Research, vol. 572, pp. 291–295 (1992).

Farhat et al., "Stress Induces Neuronal death in the hippocampus of castrated rats", Journal of Pharmatology and Experimental Therapeutics, vol. 261, pp. 686–691 (1992).

Siesjo, Bo K., M.D., "Pathophysiology and treatment of focal Cerebral ischemia," Neurosurgery, vol. 7, pp. 169–184. Part 1 and Part 2 (1993).

Stock, et al., "Indentification of Estrogen Receptor mRNA and Estrogen Modulation of Parathyroid Hormone–Stimulated Cyclic AMP Accumulation in Opossum Kidney Cells"; Journal of Cellular Physiology, vol. 150, pp. 517–525 (1992).

Weiland et al., "Estradiol Selectively Regulates Agonist Binding Sites on the N–Methyl–D–Aspartate Receptor Complex in the CA1 Region of the Hippocampus," Endocrinology, vol. 131, pp. 662–668 (1992).

Wong et al., "Long term and Short Term Electrophysiological Effects of Estrogen on the Synaptic Properties of Hippocampal CA1 Neurons"; The Journal of Neuroscience, vol. 12(8), pp. 3217–3225 (1992).

Woolley et al., "Estradiol Mediates Fluctuation in Hippocampal Synapse Density during the Estrous Cycle in the Adult Rat," Journal of Neuroscience, vol. 12, pp. 2549–2554 (1992).

Wren, Barry G., "The effect of oestrogen on the female cardiovascular", The Medical Journal of Australia, vol. 157 (1992).

Emerson et al., "Estrogen improves biochemical and neurologic outcome following traumatic brain injury in male rats, but not in females", Brain Research, vol. 608, pp. 95–100 (1993).

Falkeborn, Margareta et al., "Hormone Replacement Therapy and the Risk of Stroke", Arch Interna Med, vol. 153 (1993).

Finucane, et al., "Decreased Risk of Stroke Among Postmenopausal Hormone Users", Arch Intern Med. vol. 153, pp. 73–79 (1993).

Gay, et al., "Effect of Estrogen on Acidification in Osteoclasts": Biochemical and Biophysical Research Communications, vol. 192, No. 3, 1251–1259 (1993).

Hefti et al., in "Neurotrophic Factors", pp. 25–42, Loughlin et al. Eds., Academic Press Inc. (1993).

Luquin, et al., "Natural Flucuation and Gonadal Hormone Regulation of Astrocyte Immunoreactivity in Dentate Gyrus", Journal of Neurobiology, vol. 24, No. 7, pp. 913–924, (1993).

Mooradian, Arshag, "Antioxidant Properties of Steroids", Journal of Steroid Biochem. Molec. Biol., vol. 45, No. 6, pp. 503–511 (1993).

Bishop, et al., "Estradiol Treatment Increases Viability of Glioma and Neuroblastoma Cells in Vitro"., Molecular and Cellular Neurosciences vol. 5, pp. 001–006 (1994).

Evans, Glenda, et al, "The Effects of Raloxifene on Tibia Histomorphometry in Ovariectomized Rats", Endocrinology; pp. 1345–2283. (1994).

Hardy, et al., "Novel plasma membrane action of estrogen and antiestrogens revealed by their reulation of a large conductance chloride channel". FASEB J. vol. 8, pp. 760–765 (1994).

Hayashi, et al., "Biphasic effect of estrogen and neuronal constitutive nitric ocide synthase via $CA^{2+}$–calmodulin dependent mechanism$^+$", Biochemical and Biophysical Research Communications, vol. 203, No. 2, pp. 1013–1019 (1994).

Lagrange, et al., "The Potency of $\mu$–Opioid Hyperpolarization of Hypothalamic Arcuate Neurons is Rapidly Attenuated by 17β–Estradiol", The Journal of Neuroscience, vol. 14(10) pp. 6196–6204 (1994).

Levitt, M. Andrew, "Reduction of Infarct Size During Myocardial Ischemia and Reperfusion by Lazaroid U–74500A, a Nonglucocorticoid 21–Aminosteroid",Journal of Cardiovascular Pharmacology, vol. 23, pp. 136–140 (1994).

Oursler, et al., "Human giant cell tumors of the bone (osteoclastomas) are Estrogen Targen Cells": Proc. Natl. Acad. Sci. USA, vol. 91, pp. 5227–5231 (1994).

Sato, Masahiko, et al, "Dual–Energy X–ray Absorptiometry of Raloxifene Effects on the Lumbar Vertebrae and Femora of Ovariectomized Rats", Journal of Bone and Mineral Research, vol. 9, No. 5. (1994).

Singh, et al., "Ovarian steriod deprivation resluts in a reversible learning impariment and compromised cholinergic function in female Sprague–Dawley rats". Brain Research, vol. 644. pp. 305–312, (1994).

Uhler, Tara A., et al, "The Effects of Megadose Methylprednisolone and U–78517F on Toxicity Mediated by Glutamate Receptors in the Rat Neostriatum", Neurosurgery, vol. 34, No. 1, pp. 112–127 (1994).

Foegh et al., "Estrogen and Prevention of Transplant Atherosclerosis", The Journal of Heart and Lung Transplantation, Nov./Dec. (1995).

Goodwin, C. J., et al,"Microculture tetrazolium assays: a comparison between two new tetrazolium salts, XTT and MTS", Journal of Immunological Methods, vol. 179, pp. 95–103 (1995).

Lacort, Mercedes, et al, "Protective Effect of Estrogens and Catechloestrogens Against Peroxidative Membrane Damage in vitro", Lipids, vol. 30, No. 2 (1995).

Ruiz–Larrea, et al., "Effects of estrogens on the redox chemistry of iron: A possible mechanism of the antiozidant action of estrogens" Steroids, vol. 60, pp. 780–783 (1995).

Sato, Masahiko, et al, "Longitudinal and Cross–Section Analysis of Raloxifene Effect on Tibiae from Ovariectomized Aged Rats", The Journal of Pharmacology and Experimental Therapeutics, vol. 272, pp. 1252–1259. (1995).

Hung, C.J., et al, "Clinical Implication of Hormone Treatment in Postmenopausal Kidney Transplants", Transplantation Proceedings, vol. 28, No. 3 (Jun.), pp. 1548–1550 (1996).

Ayers, et al., "Estradiol–17 beta as an antioxidant; Some distinct features when compared with common fat–soluble antioxidants", Journal of Lab Clin Med, vol. 128, No. 4, pp. 367–375 (1996).

Behl, Christian, et al., "Neuroprotection against Oxidative Stress by Estrogens: Structure–Activity Relationship", Molecular Pharmacology, vol. 51, No. 4, pp. 535–541 (1997).

Kolodgie, et al., "Myocardial Protection of contractile Function After Global Ischemia by Physiologic Estrogen Replacement in the Ovariectomized Rat", Journal of Mol Cell. Cardiol, vol. 29, pp. 2403–2414 (1997).

Simpkins et al., "Estrogens may reduce mortaility and ischemic damage caused by middle cerebral artery occlusion in the female rat", Journal of Neurosurg. vol. 87, pp. 724–730; (Nov. 1997).

Shi et al., "Effects of 17B–estradiol on glucose transporter 1 expression and endothelial cell survival following focal ischemia in the rats", Exp. Brain Res. , vol. 117, pp. 200–206 (1997).

Alkayed et al., "Gender–Linked Brain Injury in Experimental Stroke", Stroke, vol. 29, pp. 159–166 (1992).

Sawada, et al., Estradiol Protects Mesencephalic Dpoaminergic Neurons From Oxidative Stress–Induced Neuronal Death; Journal of Neuroscience Research vol. 54 707–719 (1998).

Shi et al. Estrogen attenuates over–expression of β–amyloid precursor protein messenger RNA in an animal model of focal ischemia; Brain Research 810: 87–92 (1998).

Wang, et al., Estrogen Provides Neuroprotection in Transient Forebrain Ischemia Through Perfusion –Independent Mechanisms in Rats; Stroke; 30: 630–637 (1999).

Yang et al., "Estradiol Exerts Neuroprotective Effects When Administered After Ischemic Insult,"Stroke; vol. 31; 745–750 (2000).

Green, P.S., et al., The Nonfeminizing Enantiomer of 17 beta Estradiol Exerts Protective Effects in Neuronal Cultures and a Rat Model of Cerebral Ischemia; Endocrinology vol. 142; No. 1 400–406; (2001).

* cited by examiner $C_{16}H_{22}O_2$
MW = 246

[2S-(2α,4aα,10aβ)]-1,2,3,4,4a,9,10,10a-OCTAHYDRO-7-HYDROXY-2-METHYL-2-PHENANTHRENEMETHANOL $C_{16}H_{20}O_2$
MW = 244

[2S-(2α,4aα,10aβ)]-1,2,3,4,4a,9,10,10a-OCTAHYDRO-7-HYDROXY-2-METHYL-2-PHENANTHRENECARBOXALDEHYDE

| | Name[1] | % of 3,17β-Estradiol Neuroprotection |
|---|---|---|
| R=H | 3,17β-Estradiol | 100* |
| R=CH₃ | 3,17β-Estradiol 3-O-ME | -2 |
| R=H | Estratriene-3-ol | 103*[2] |
| R=H | 3,17α-Estradiol | 81* |
| R=CH₃ | 3,17α-Estradiol 3-acetate | -20 |
| R=H | 2-Hydroxy-3,17β-Estradiol | 70* |
| R=CH₃ | 3,17β-Estradiol 2,3-O-ME | 7 |
| R=H | Estrone | 58* |
| R=CH₃ | Estrone 3-O-ME | -11 |
| R=H | Estriol | 46* |
| R=CH₃ | Estriol 3-O-ME | 2 |
| R=H | Ethynyl Estradiol | 41* |
| R=CH₃ | Mestranol | -6 |

FIG. 14

| Structure | NAME | % OF 17β-ESTRADIOL NEUROPROTECTION |
|---|---|---|
|  | 3,17β-ESTRADIOL | 100* |
|  | PHENOL | -27 |
|  | DIETHYLSTILBESTEROL | 74* |
|  | DIETHYLSTILBESTEROL-MONO-O-ME | 60* |
|  | DIETHYLSTILBESTEROL-DI-O-ME | 2 |

*$p<0.05$ VS SERUM-FREE CONTROL GROUPS

CYTOPROTECTIVE EFFECT OF POLYCYCLIC PHENOLIC COMPOUNDS

CROSS REFERENCE

This application is a continuation-in-part of application Ser. No. 09/129,209, now U.S. Pat. No. 6,197,833 filed Aug. 4, 1998, now U.S. Pat. No. 6,197,833 which is a division of U.S. application Ser. No. 08/685,574, filed Jul. 24, 1996, now U.S. Pat. No. 5,859,001; and application U.S. Ser. No. 09/128,862, filed Aug. 4, 1998, which is a division of U.S. application Ser. No. 08/782,883, filed Jan. 10, 1997 now U.S. Pat. No. 5,874,672; and application Ser. No. 09/179,640 filed Oct. 27, 1998, which is a division of U.S. application Ser. No. 08/749,703 filed Nov. 15, 1996, now U.S. Pat. No. 5,877,169, (the above being incorporated by reference) which is continuation-in-part of Ser. No. 685,574 filed Jul. 24, 1996, now U.S. Pat. No. 5,859,001 and Ser. No. 08/648,857 filed May 16, 1996, now U.S. Pat. No. 5,843,934, which is a division of Ser. No. 08/318,042, filed Oct. 4, 1994 now U.S. Pat. No. 5,554,601 which is a continuation-in-part of Ser. No. 08/149,175, filed Nov. 5, 1993, abandoned.

TECHNICAL FIELD

The present invention relates to novel compositions and methods for the protection of tissues, cells, and organs both in vivo and in vitro.

BACKGROUND

Degenerative diseases and aging are characterized by a broad spectrum of symptoms which vary in severity and range from individual to individual.

A common feature of degenerative disorders and diseases, trauma and the process of aging in animals is the progressive damage to cells and consequently tissues and organs. This damage may be caused by an external agent and may act in combination with internal cellular processes. Cell death may occur by necrotic or apoptotic mechanisms. For example, ischemia, which may occur as a result of stroke, heart disease or a transplantation event, arises from a cut-off in oxygen and nutritional supply to tissues which results in extensive cell damage. Treatments to minimize cell, tissue and organ damage would be helpful to ameliorate the consequences of ischemic events. Other examples where cell protection is desirable include the brain where damaged neurons and supporting structures are associated with neurodegenerative diseases that give rise to conditions such as Alzheimer's disease. In the heart, damaged muscle and endothelial cells are associated with cardiovascular disease. In bone, osteoporosis is associated with damaged osteocytes and osteoblasts. Treatments to modulate cell death associated with such conditions could be of significant benefit to an aging population.

The absence of an effective cytoprotective therapy can result in either loss of life or a general decline in the quality of life including permanent disability with high health care costs to patients, their families and the health care providers.

SUMMARY

The invention provides a method for conferring a cytoprotective effect on a population of cells that includes: providing a polycyclic phenolic compound in a physiologically acceptable formulation; and administering the formulation in an effective dose to the population of cells to confer cytoprotection.

In a preferred embodiment of the invention, a method for conferring cytoprotection in a population of cells in a subject is provided that includes: providing an effective dose of a polycyclic phenolic compound in a pharmaceutical formulation; and administering the formulation in an effective dose to the subject to confer cytoprotection.

BRIEF DESCRIPTION OF THE DRAWINGS

These and other features, aspects and advantages of the present invention will become better understood with reference to the following description, appended claims and accompanying drawings where:

FIG. 14 shows the loss of cytoprotection, in comparison to 17β-estradiol, of certain compounds containing substitutions at the #3 position of the A ring.

DETAILED DESCRIPTION

We have shown that polycyclic phenolic compounds including estrogen compounds act effectively in a variety of cell types to protect cells from damage and death in conditions where intrinsic or extrinsic damage has occurred.

An "animal subject" is defined here and in the claims as inclusive of human subjects.

The term "polycyclic phenolic compounds" used here and in the claims refer to a class of compounds having (a) two or more ring structures in the compound; and (b) a terminal phenolic ring. In a preferred embodiment, these compounds have a size range less than 1000 Daltons, more preferably larger than 170 Daltons. This definition includes the compounds' salts, derivatives, enantiomers and diasteromers. The polycyclic phenolic compounds of the invention may be formulated in a physiologically acceptable formulation in a manner that is consistent with the art and administered in an effective dose vivo or in vitro to provide a cytoprotective effect. Examples of compounds that fit the above description are described below.

The term "cytoprotection" is defined here and in the claims as the slowing, halting or prevention from deterioration and death of a cell or a population of cells. Such deterioration and death may be precipitated by one or more external factors or by intrinsic factors including apoptosis or by a combination of such factors. A population of cells includes cell cultures, tissues or organs.

Figure 8:
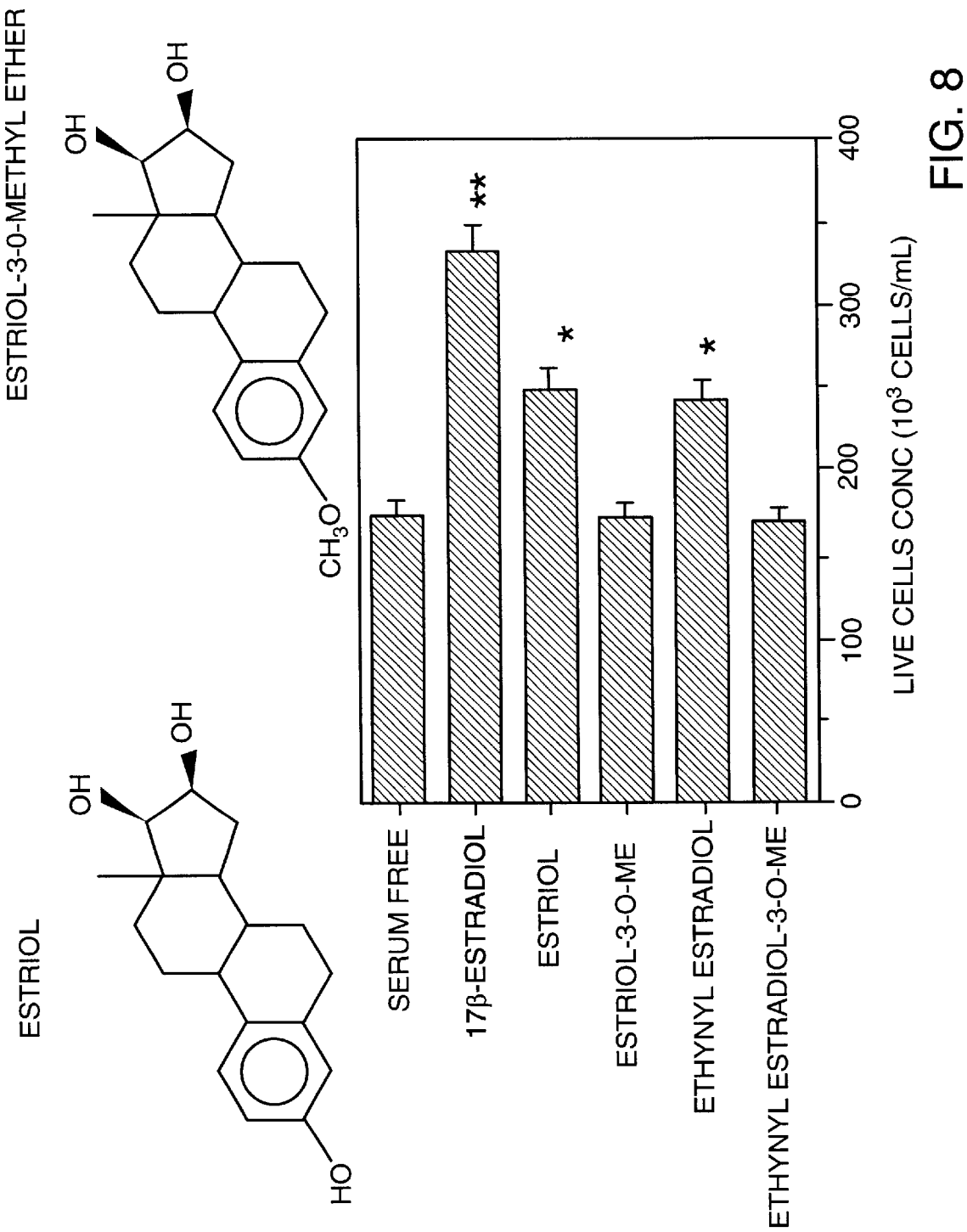
FIG. 8 shows the cytoprotective effects of five compounds on SK-N-SH cells following serum deprivation. The polycyclic phenolic compounds, 17β-estradiol, estriol and ethynyl estradiol, were highly protective in contrast to estriol-3-o-methyl and ethynyl estradiol-3-o-methyl.
Figure 9:
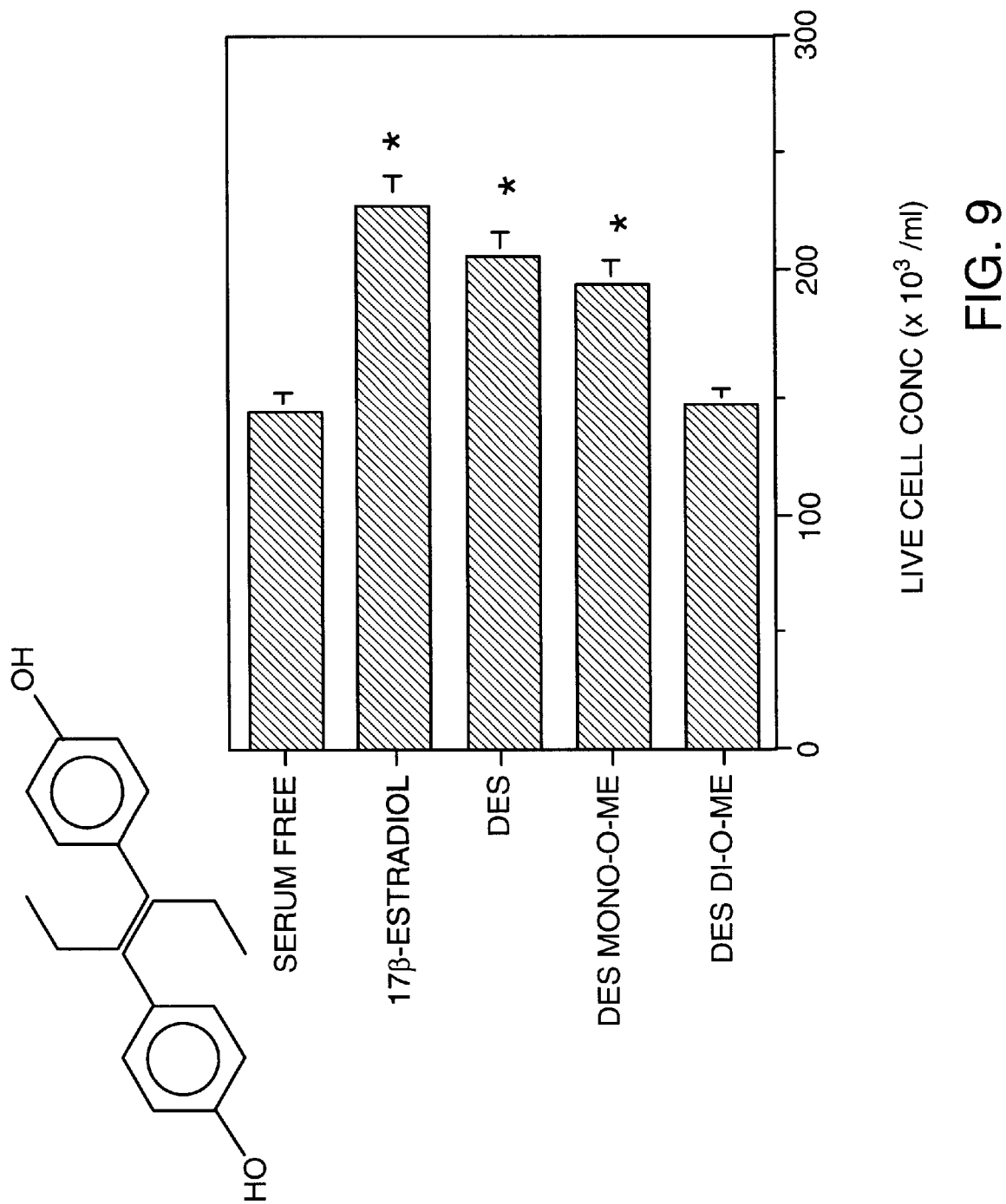
FIG. 9 shows the cytoprotective effects of four compounds on SK-N-SH cells following serum deprivation. The polycyclic phenolic compounds, 17β-estradiol, diethylstilbestrol and diethylstilbestrol-mono-O-methyl were highly protective in contrast to diethylstilbestrol-di-O-methyl.
Figure 15:
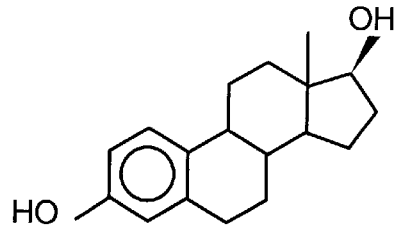
FIG. 15 shows the cytoprotectivity of 17β-estradiol, phenol and diphenols.
Figure 15:
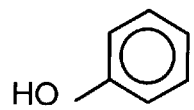
Figure 15:
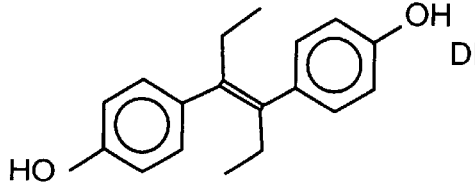
Figure 15:
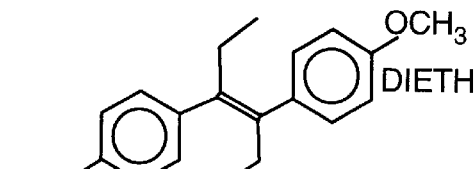
Figure 15:
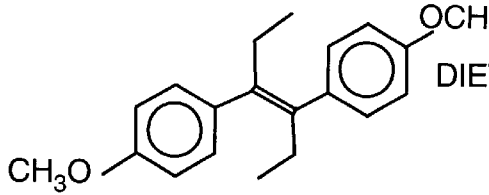

The class of cytoprotective compounds described here includes (a) compounds that are characterized by two-carbon rings (eg., see FIGS. 9, 13 and 15); (b) compounds that are characterized by three-carbon rings (eg., see FIGS. 10, 11, 12 and 13); compounds that are characterized by 4-carbon rings (eg., see FIGS. 6, 7, 8, 9, 13, 14). Cytoprotective compounds may further comprise 5-carbon rings or more. Cytoprotective compounds may be steroidal or non-steroidal.

In an embodiment of the invention, cytoprotection is provided at an effective dose using low concentrations of a polycyclic phenolic compound in culture fluid or in body fluids. More specifically, a cytoprotective effect can be achieved at plasma concentrations of 200 nM or less and greater than 0.1 nM, more particularly between 0.1 nM and 2 nM. The relatively low effective dose of cytoprotective compounds capable of causing a cytoprotective effect according to the invention, is in stark contrast with the findings of others who have tested estrogens in in vitro assays. For example, Droescher et al. (PCT WO 95/13076; DE94/01309) describe an $IC_{50}$ of 12.8 $\mu$M estrogen to inhibit free radical oxidation in a lipid peroxidation assay. The indirect lipid peroxidation assay for cell protection used by Droescher et al. is a biochemical assay and is not comparable to the cell assays used in the invention to directly measure a cellular response. Consequently, the two assays cannot be directly compared and the results of one assay cannot be extrapolated to the other. The advantage of the cytoprotection assay used here is that live and dying cells are utilized to determine cytoprotection directly.

It is desirable that the amount of a cytoprotective agent to be used to treat a subject should be within the range that is relatively non-toxic to the patient especially when the compound is used long-term. According to the invention, cytoprotection has been obtained in cell cultures at concentrations of 2 nM with a variety of different polycyclic phenolic compounds. Furthermore, in addition to neuronal cells, significant cytoprotection has been demonstrated to occur in a range of cell types including skeletal muscle (Example 1), erythrocytes (Example 3) cardiomyocytes (Example 4) and endothelial cells (Example 5).

According to the invention, a phenolic structure on a terminal ring is required for cytoprotection. Any modification whatsoever to the structure or terminal phenolic group would be consistent with cytoprotection according to the invention so long as the phenolic structure of the terminal ring is maintained. Compounds such as progesterone and corticosterone, for example, which lack a hydroxyl group on a terminal ring and therefore do not have a terminal phenolic ring, show little or no cytoprotection. Effective cytoprotection can be achieved with structures containing a hydroxyl group on any available carbon in the terminal ring, so long as the phenolic structure of that ring is preserved. Following replacement of the #3 position hydroxyl group on the terminal phenolic group with, for example, a methyl group, a significant loss of cytoprotective properties of the compound was observed (FIGS. 6, 7, 8, 9, 11 and 14). According to the invention, any modifications resulting in loss of the phenolic structure of the terminal ring would result in loss of cytoprotection activity.

According to embodiments of the invention, cytoprotective compounds for use in the method of the invention may have an R group substitution on any available carbon on the terminal phenolic ring within the limitation described above or on carbons in one or more of the other rings of the structure. These R groups may be present in α or β isomeric configurations. The R groups may be selected from inorganic or organic atoms or molecules. Below, examples of a number of different types of R groups have been provided although the invention is not limited by these examples.

The R group may include any inorganic R group including any of a halogen, an amide, a sulfate, a nitrate, fluoro, chloro, or bromo groups. Additionally, R groups selected from sodium, potassium and/or ammonium salts may be attached to the α or β positions to replace hydrogen on any available carbon in the structure. The R group may be organic or may include a mixture of organic molecules and ions. Organic R groups may include alkanes, alkenes or alkynes containing up to six carbons in a linear or branched array. For example, additional R group substituents may include methyl, ethyl, propyl, butyl, pentyl, hexyl, heptyl, dimethyl, isobutyl, isopentyl, tert-butyl, sec-butyl, isobutyl, methylpentyl, neopentyl, isohexyl, hexenyl, hexadiene, 1,3-hexadiene-5-yne, vinyl, allyl, isopropenyl, ethynyl, ethylidine, vinylidine, isopropylidene; methylene, sulfate, mercapto, methylthio, ethylthio, propylthio, methylsulfinyl, methylsulfonyl, thiohexanyl, thiobenyl, thiopenol, thiocyanato, sulfoethylamide, thionitrosyl, thiophosphoryl, p-toluenesulfonate, amino, imino, cyano, carbamoyl, acetamido, hydroxyamino, nitroso, nitro, cyanato, selecyanato, arccosine, pyridinium, hydrazide, semicarbazone, carboxynethylamide, oxime, hydrazone, sulfurtrimethylammonium, semicarbazone, o-carboxymethyloxime, aldehyde hemiacetate, methylether, ethylether, propylether, butylether, benzylether, methylcarbonate, carboxylate, acetate, chloroacetate, trimethylacetate, cyclopentylpropionate, propionate, phenylpropionate, carboxylic acid methylether, formate, benzoate, butyrate, caprylate, cinnamate, decylate, heptylate, enanthate, glucosiduronate, succinate, hemisuccinate, palmitate, nonanoate, stearate, tosylate, valerate, valproate, decanoate, hexahydrobenzoate, laurate, myristate, phthalate, hydroxyl, ethyleneketal, diethyleneketal, formate, chloroformate, formyl, dichloroacetate, keto, difluoroacetate, ethoxycarbonyl, trichloroformate, hydroxymethylene, epoxy, peroxy, dimethyl ketal, acetonide, cyclohexyl, benzyl, phenyl, diphenyl, benzylidene, and cyclopropyl groups. R groups may be attached to any of the constituent rings to form a pyridine, pyriazine, pyrimidine, or v-triazine. Additional R group substituents may include any of the six member or five member rings itemized below.

Any compound may have, in addition to the phenolic A ring, a heterocyclic carbon ring which may be aromatic or non-aromatic with any of the substitutions described above and further may be selected from, for example, one or more of the following structures: phenanthrene, naphthalene, napthols, diphenyl, benzene, cyclohexane, 1,2-pyran, 1,4-Pyran, 1,2-pyrone, 1,4-pyrone, 1,2-dioxin, 1,3-dioxin (dihydro form), pyridine, pyridazine, pyrimidine, pyrazine, piperazine, s-triazine, as-triazine, v-triazine, 1,2,4-oxazine, 1,3,2-oxazine, 1,3,6-oxazine(pentoxazole), 1,2,6 oxazine, 1,4-oxazine, o-isoxazine, p-isoxazine, 1,2,5-oxathiazine, 1,2,6-oxathiazine, 1,4,2-oxadiazine, 1,3,5,2-oxadiazine, morpholine (tetrahydro-p-isoxazine), any of the six ringed structure listed above being a terminal group in the compound. Additionally, any of the above carbon ring structure may be linked directly or via a linkage group to any further heterocyclic aromatic or non-aromatic carbon ring including: furan; thiophene(thiofuran); pyrrole(azole); isopyrrole (isoazole); 3-isopyrrole(isoazole); pyrazole(1,2-daizole); 2-isoimidazole(1,3-isodiazole); 1,2,3-triazole; 1,2,4 triazole; 1,2-diothiole; 1,2,3-oxathiole; isoxazole(furo(a) monozole); oxazole(furo(b)monazole); thiazole; isothiazole; 1,2,3-oxadiazole; 1,2,4-oxadiazole; 1,2,5-oxadiazole; 1,3,5 oxadiazole; 1,2,3,4-oxatriazole; 1,2,3,5-oxatriazole; 1,2,3-dioxazole; 1,2,4-dioxazole; 1,3,2-dioxazole; 1,3,4-dioxazole; 1,2,5-oxathiazole; 1,3-oxathiole; cyclopentane. These compounds in turn may have associated R groups selected from the examples above that are substituted on a carbon ring at any of the available sites.

Polycyclic phenolic compounds may form a cyclopentanophen(a)anthrene ring compound and which, for example, may be selected from the group consisting of 1,3,5(10),6,8-estrapentaene, 1,3,5(10),6,8,11-estrapentaene, 1,3,5(10)6,8,15-estrapentaene, 1,3,5(10),6,-estratetraene, 1,3,5(10),7-estratetraene, 1,3,5(10)8-estratetraene, 1,3,5(10) 16-estratetraene, 1,3,5(10)15-estratetraene, 1,3,5(10)-estratriene, 1,3,5(10)15-estratriene.

Polycyclic phenolic compounds include raloxifene, tamoxifen, androgenic compounds, and their salts where an intact terminal phenolic ring is present.

Polycyclic phenolic compounds include any compound in the form of a prodrug, that may be metabolized to form an active polycyclic phenolic compound having cytoprotective activity.

Administration of any of the compounds of the invention may include the use of a single compound or a mixture of cytoprotective compounds. Treatment may be administered in vivo that is to the patient or ex vivo to a sample of isolated tissue outside the body which is destined for transplantation. The treated subject or tissue protected according to the invention is not species-restricted but may be applied to tissue from any animal, including any mammal, such as domestic animals, for example, pigs, cows and sheep, as well as primates including humans.

Where the cytoprotective compound is administered to a subject, the recommended route of administration includes oral, intramuscular. transdermal, nasal, buccal, intravenous, rectal and subcutaneous. Methods of administering the compound of the invention may be by unit dose or by controlled release vehicles.

The use of cytoprotective compounds of the invention results in an improved outcome for cell, organ, and tissue transplantation by reducing the damage to the tissue that leads to decreased viability of the cells. The cytoprotective compounds of the invention may be used to treat various degenerative diseases so as to slow the progression of the disease.

Tissues that are protected by the method of the invention may be derived from children, adult or fetuses and include, but are not limited to, stem cells, blood and all of its components, including erythrocytes, leukocytes, platelets and serum, central nervous tissue, including brain and spinal cord tissue, neurons, and glia; peripheral nervous tissue, including ganglia, posterior pituitary gland, adrenal medulla, and pineal; connective tissue, skin, ligaments, tendons, and fibroblasts; muscle tissue, including skeletal, smooth and cardiac tissues or the cells therefrom; endocrine tissue, including anterior pituitary gland, thyroid gland, parathyroid gland, adrenal cortex, pancreas and its subparts, testes, ovaries, placenta, and the endocrine cells that are a part of each of these tissues; blood vessels, including arteries, veins, capillaries and the cells from these vessels: lung tissue; heart tissue and whole organ; heart valves; liver; kidney; intestines; bone, including osteocytes, osteoblasts and osteoclasts; immune tissue, including blood cells, bone marrow and spleen; eyes and their parts; reproductive tract tissues; or urinary tract tissue.

Examples of degenerative diseases, disorders and conditions that may be treatable by a cytoprotective agent include: neurological and neurodegenerative diseases and conditions such as Alzheimer's disease, Parkinson's disease, amyotrophic lateral sclerosis (ALS), multiple sclerosis, peripheral neuropathy, shingles, stroke, traumatic injury, various neurological and other degenerative consequences of neurological and chest surgeries, schizophrenia and epilepsy, Down's Syndrome, Turner's Syndrome, degenerative conditions associated with AIDS, various bone disorders including osteoporosis, osteomyclitis, ischemic bone disease, fibrous dysplasia, rickets, Cushing's syndrome and osteoarthritis, other types of arthritis and conditions of connective tissue and cartilage degeneration including rheumatoid, psoriatic and infectious arthritis, various infectious diseases, muscle wasting disorders such as muscular dystrophy, skin disorders such as dermatitis, eczema, psoriasis and skin aging, degenerative disorders of the eye including macular degeneration and retinal degeneration, disorders of the ear such as otosclerosis, impaired wound healing, various diseases and conditions of the heart including cardiac ischemia, myocardial infarction, chronic or acute heart failure, cardiac dysrhymias, artrial fibrillation, paroxymial tachycardia, ventricular fibrillation and congestive heart failure, circulatory disorders including atherosclerosis, arterial sclerosis and peripheral vascular disease, diabetes (Type I or Type II), various diseases of the lung including pneumonia, chronic obstructive lung disease (bronchitis, emphysemia, asthma), disorders of the gastrointestinal tract such as ulcers and hernia, dental conditions such as periodontitis, liver diseases including hepatitis and cirrhosis, pancreatic ailments including acute pancreatitis, kidney diseases such as acute renal failure and glomerulonepritis, various blood disorders such as vascular amyloidosis, aneurysms, anemia, hemorrhage, sickle cell anemia, autoimmune disease, red blood cell fragmentation syndrome, neutropenia, leukopenia, bone marrow aphasia, pancytopenia, thrombocytopenia, hemophilia. The preceding list of diseases and conditions which are potentially treatable with a cytoprotective agent is not intended to be exhaustive or limiting but presented as examples of such degenerative diseases and conditions.

The cytoprotective compounds of the invention include, but are not limited to, the class of polycyclic phenolic compounds containing the cyclopentanophen(a)anthrene ring structure that are steroidal in structure as well as related classes of compounds that contain a phenolic ring but are non-steroidal in structure. Compounds that are non-steroidal and have a terminal phenolic ring and at least one additional carbon ring structure are cytoprotective and include three-ring compounds (FIGS. 10, 11, 12 and 13) such as exemplified by [2S-(2a,4aα,10αβ)]-1,2,3,4,4a,9,10,10a-octahydro-7hydroxy-2-methyl-2-phenanthrenemethanol (PAM) and [2S-(2a,4aα,10αβ)]-1,2,3,4,4a,9,10,10a-octahydro-7hydroxy-2-methyl-2-phenanthrenecarboxyaldehyde (PACA) have been demonstrated to have a cytoprotective effect (see FIG. 10 and 11). The structure of these compounds is shown in FIG. 12. Two namomolar concentrations of either PAM or PACA were found to permit an increase in cell survival of about 15%.

Phenol in the absence of other agents is not cytoprotective (FIG. 15) nor are straight chain substitutions of phenolic compounds. However, a compound having a terminal phenolic ring and at least one other carbon ring is cytoprotective. For example, the non-fused two-ring structure, diethylstilbestrol, has demonstrated cytoprotective properties according to the invention (FIG. 9 and 15). This compound has a terminal phenolic ring structure that is associated with a second phenolic ring via a linkage group. Removal of the hydroxyl group on the terminal phenolic ring results in a loss of cytoprotective activity.

According to the invention, it has been shown that a polycyclic phenolic compound when administered to the donor animal prior to surgery enhances the viability of the cells after their removal. Example 1demonstrates the beneficial effect of pretreating a rat with 17β-estradiol prior to removal of muscle tissue. Once samples are isolated, polycyclic phenolic compounds have been shown to protect erythrocytes (red blood cells) from death induced by $FeCl_3$ induced oxidative distress. (Example 3). The beneficial effect of pretreating the recipient animal with a polycyclic phenolic compound prior to implantation of tissue has been demonstrated in Example 2, where pretreatment of the animal recipient (rat) with 17β-estradiol enhances the viability of the transplanted neuronal cells during reperfusion. Protective effects of polycyclic phenolic compounds on cardiac myocytes and brain endothelial cells are illustrated in Examples 4 and 5 respectively. The cytoprotective effects of maintaining cells (SK-N-SH neurons) in the presence of an estrogen compound in vitro has been demonstrated in Example 1 and Example 2 of Ser. No. 08/685,574, now U.S. Pat. No. 5,859,001, incorporated herein by reference.

EXAMPLES

Example 1

In vivo Demonstration of the Cytoprotective Effect of Polycyclic Phenolic Compounds on Skeletal Muscle This example demonstrates the beneficial effect of pretreating a subject with a polycyclic phenolic compound prior to removal of cells, tissues or organs. In particular, rats were treated in vivo with a polycyclic phenolic compound prior to removal of muscle tissue from the animal. The status of the isolated muscle tissue was followed by measuring cumulative levels of creatine kinase in the isotonic medium in which the muscle was subsequently maintained. Creatine kinase is a muscle-specific enzyme which is a marker of damaged tissue.

Adult female Charles River CD rats were ovariectomized and implanted subcutaneously with 5mm silastic pellets containing 17β-estradiol (treatment group). A second group of animals was left intact (non-ovariectomized) and implanted with empty silastic pellets (sham group). A third group of animals was ovariectomized but not treated with silastic pellets or 17β-estradiol (ovx group). Silastic pellets were prepared and inserted according to the method described by Singh et al. (1994) Brain Res. 644: 305–312. Serum estradiol levels at the end of a two week period following pellet insertion were 20.0, 32.3 and 56.5 pg/ml for the ovx group, sham group and treatment groups, respectively.

Two weeks after the silastic pellets were inserted (or an equivalent period of time in the case of oxv group animals), the animals were humanely sacrificed and the soleus muscles harvested via the tendons were placed into a carboxygenated balanced salt solution (pH 7.4) at 37°. Damage to the muscle tissue was assessed by the cumulative release of creatine kinase in vitro over a four hour period.

Figure 1:
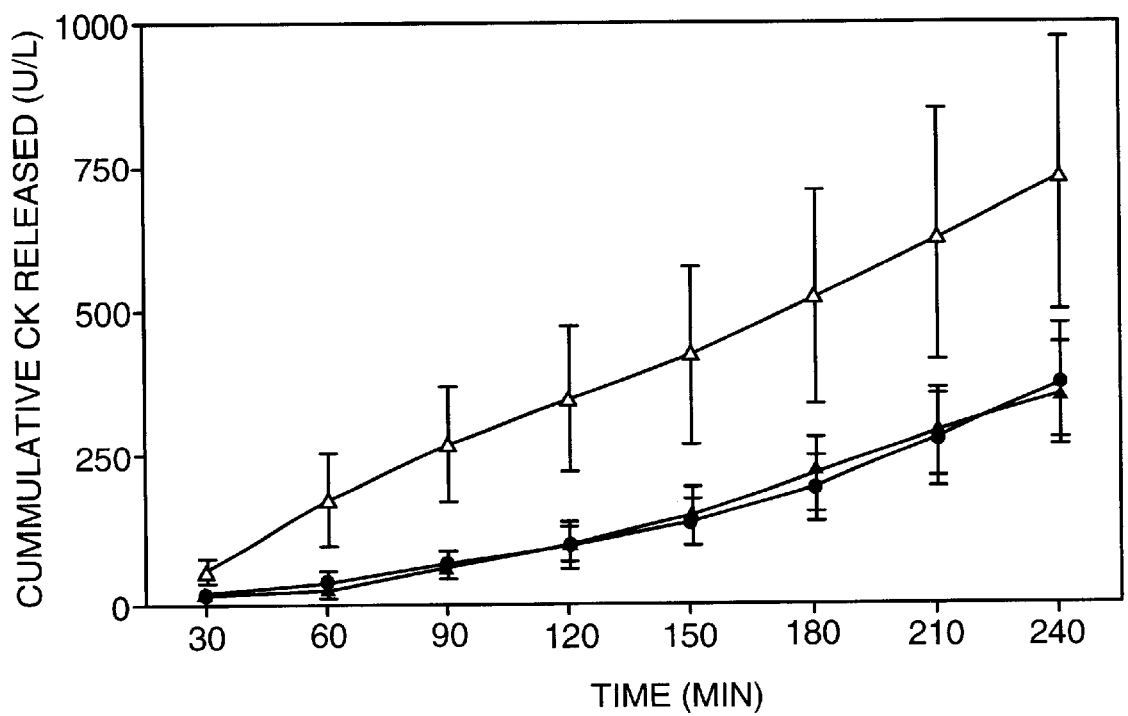
FIG. 1 shows cumulative creatine kinase (CK) released from soleus muscle as a function of time after muscles were placed in a tissue bath. Open triangles indicate samples from ovariectomized animals, closed circles indicate samples from ovary-intact sham treated animals, closed triangles indicate samples from 17β-estradiol replaced ovariectomized animals. These data show that muscle excised from non-treated ovariectomized rats released significantly more creatine kinase, and hence show much greater cellular damage, than those from either ovary-intact or estrogen-replaced ovariectomized animals.

FIG. 1 show the results. Open triangles indicate ovx group, closed circles indicate sham group, closed triangles indicate treatment group. The mean plus and minus the standard error of the mean (±SEM) are depicted. As shown in FIG. 1, the cumulative release of creatine kinase from the soleus muscle of the ovx group animals was significantly higher compared to both sham group animals and treatment group animals. At the end of the four hour incubation period, to eliminate any potential discrepancies in cytosolic enzyme release as a function of total muscle creatine kinase, the muscles were homogenized and total remaining enzyme activity measured. There was no statistical difference among the treatment groups with respect to total muscle creatine kinase.

The results of Example 1 illustrate the protective effect of polycyclic phenolic compounds on skeletal muscle.

Figure 2A:
FIGS. 2A and B show a photomicrograph (4×magnification) of brain sections containing SK-N-SH cells implanted into the corpus callosum of ovariectomized rats. Sections were obtained at one week following cellular transplantations. Panel A shows a section from an animal treated with an empty silastic pellet. Panel B shows a section from an animal treated with a silastic pellet containing 17β-estradiol in which an outgrowth of cells was observed indicating cell viability.
Figure 2B:
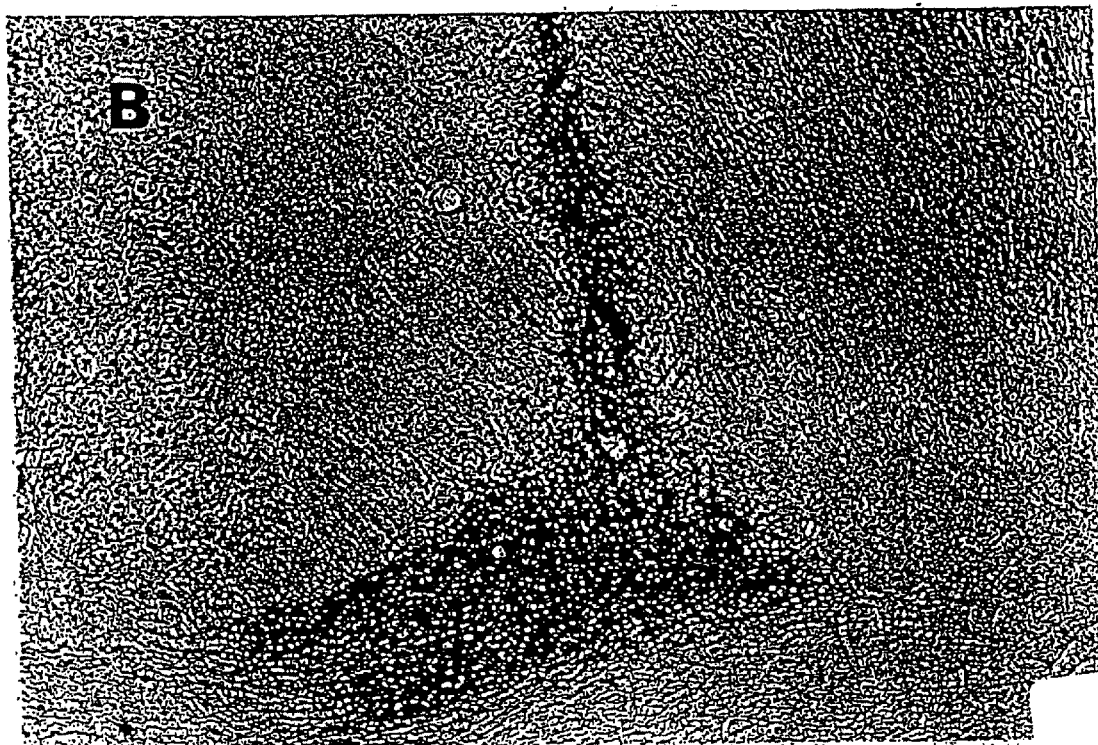

Example 2
In vivo Demonstration of the Cytoprotective Effect of Polycyclic Phenolic Compounds on Neuronal Cells This example demonstrates the beneficial effect of pretreating a subject with a polycyclic phenolic compound prior to implantation of cells, tissue or organs from an external source. In particular, rats were treated with a polycyclic phenolic compound prior to introduction of an implant of neuronal SK-N-SH cells. The status of the implanted neuronal cells was determined by observing histological sections of the brain after sacrifice of the animals (FIG. 2).

The ability of a polycyclic phenolic compound to protect tissue during reperfusion in the recipient was determined as follows.

Adult female Charles River CD rats were ovariectomized and implanted with an empty silastic tube (sham group) or with a silastic tube containing 17β-estradiol (treatment group). One week later both sham and treatment groups were subjected to a neurosurgical implantation of SK-N-SH human neuronal cells into the corpus callosum. Prior to implantation, the SK-N-SH cells had been grown in vitro in the absence of steroid hormones. The animals were sacrificed at 1 week after implantation and the brains were surgically removed, cut into 4 μM sections and stained with cresyl violet.

In sham animals, SK-N-SH cells were observed to be clumped at the injection site and at various other locations. By contrast, in treatment group animals the SK-N-SH cells were well distributed without clumping of cells. The clumping of cells represents a lack of success of the transplantation inasmuch as these clumped cells are not interacting with the host tissue due to their lack of viability. By contrast, SK-N-SH cells transplanted into treatment group rats appeared to grow out from the injection site.

The beneficial effect of treating the recipient with a polycyclic phenolic compound exemplified by 17β-estradiol, prior to receipt of transplanted tissue, was thus established. The experimental method disclosed in this example may be used in a routine manner to test any selected polycyclic phenolic compound.

Example 3
In vitro Demonstration of the Cytoprotective Effect of Polycyclic Phenolic Compounds on Erythrocytes The ability of polycyclic phenolic compounds to protect cells in vitro following their removal from a human subject was demonstrated using isolated red blood cells (erythrocytes). The cells were exposed to $FeCl_3$ which is an toxic oxidizing agent and creates conditions commonly encountered by tissues and organs when removed from the host. This condition is particularly relevant to tissues with a high iron content such as erythrocytes and spleen cells.

Figure 3:
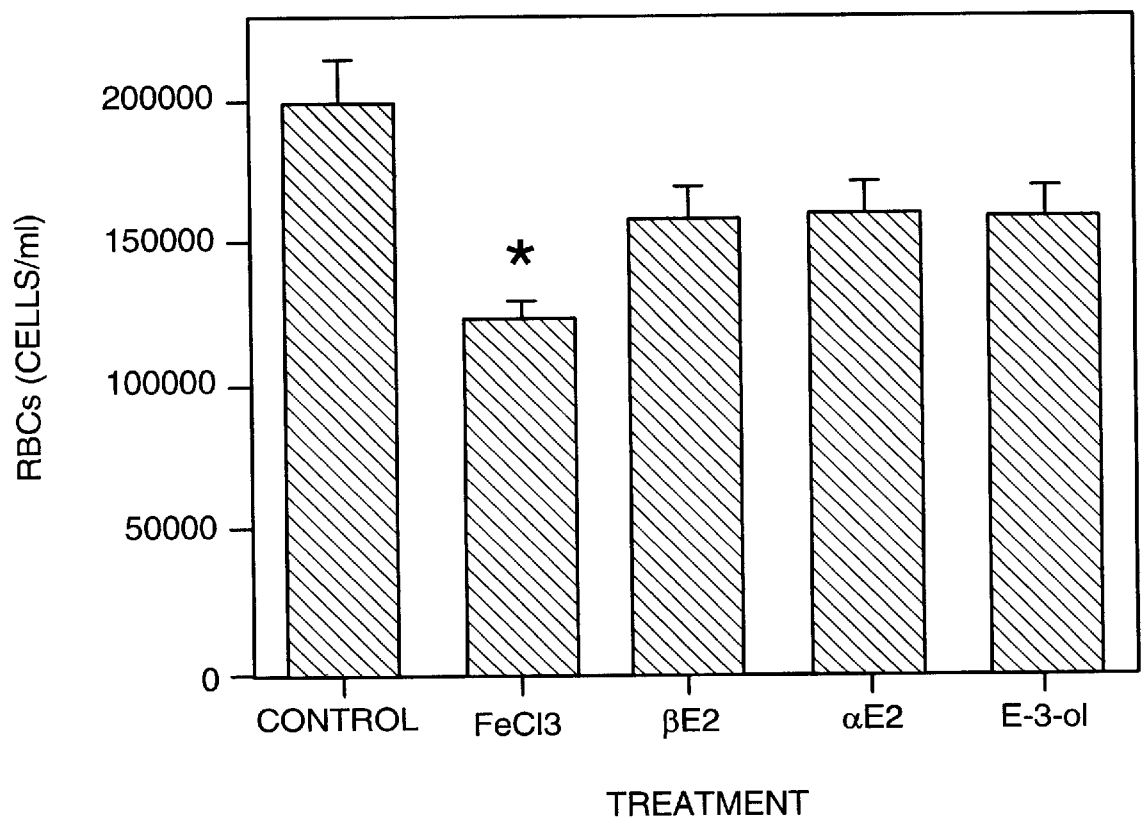
FIG. 3 shows the toxic effect of an oxidizing agent, $FeCl_3$, on the viability of red blood cells and the cytoprotective effect of three polycyclic phenolic compounds, 17β-estradiol, 17α-estradiol and estratriene-3-ol. Each of the polycyclic phenolic compounds had significant cytoprotective effect on red blood cells.

Blood samples were withdrawn from an adult male human subject and centrifuged to collect erythrocytes. The erythrocytes were then washed with isotonic physiological saline. Cells were then incubated with 200 μM $FeCl_3$ or with 200 μM $FeCl_3$ in the presence of 20 nM 17β-estradiol (βE2), 17α-estradiol (αE2) or estratriene-3-ol (E-3-ol) for 4 hours at 37° C. At the end of a 4 hour incubation period the remaining cells were counted. Cells without $FeCl_3$ treatment served as controls. As shown in FIG. 3, treatment with $FeCl_3$ reduced erythrocyte numbers by 42% versus untreated controls (the asterisk indicates that the p value is less than 0.05, which means that the data are statistically significant). By contrast, erythrocytes treated with 17β-estradiol, 17α-estradiol or estratriene-3-ol failed to exhibit a significant reduction in cell numbers in response to $FeCl_3$ treatment.

These results demonstrate that in vitro treatment of erythrocytes with polycyclic phenolic compounds provides protection from oxidative stress-induced cell death.

Example 4
In vitro Demonstration of the Cytoprotective Effect of Polycyclic Phenolic Compounds on Cardiac Myocytes This example demonstrates the cytoprotective effect of polycyclic phenolic compounds on cardiac myocyte cells which were maintained in culture and exposed to adverse conditions. Cells treated with either a combination of glucose deprivation and hypoxia or glucose deprivation alone were significantly protected from death by polycyclic phenolic compounds, thereby demonstrating the beneficial effect of treating a subject so as to preserve cardiac cells and tissue.

H9c2 cardiac myocyte cells were obtained from American Type Tissue Collection (Rockville, Md.). Cells were between passages 11–15 when obtained, although the passage number is not considered to be relevant to the experiment. Smaller or larger passage numbers, or primary cells, would be expected to yield similar results. Cells were maintained in DMEM medium (GIBCO, Gaithersburg, Md.) supplemented with 10% charcoal-stripped fetal bovine serum (obtained from Hyclone, Logan, Utah) at 37° C. under 10% $CO_2$/90% air using standard culture techniques.

When the experiment was initiated, media was replaced with glucose-free, serum-free DMEM with hydroxypropyl-β-cyclodextrin (HPCD)-encapsulated 17β-estradiol, HPCD-encapsulated 17α-estradiol or HPCD as the vehicle control. HPCD and encapsulated 17β-estradiol were purchased from Sigma and 17α-estradiol was encapsulated according to the procedure of Brewster et al (1990) Reviews Neuroscience 2: 241–285. Steroids were used at a final concentration of 2 nM or 200 nM. Dishes were immediately placed in a modular incubator chamber. The chamber was flushed with 100% $N_2$ for 15 min to achieve hypoxic conditions and the cells were incubated in the chamber for 12 hr at 37° C. Cells were then returned to 10% $CO_2$/90% air for 12 hr before viability assessment. Viability was assessed by exposing cells to 1 μM Calcein AM (Molecular Probes, Eugene, Oreg.) and 1 μg/ml propidium iodide (Molecular Probes, Eugene, Oreg.) in phosphate buffered saline (pH 7.4) for 15 minutes. Cells were visualized using a fluorescent Nikon® microscope and two random fields were photographed. Live cells were distinguished by the presence of a bright green fluorescence and the absence of nuclear staining by propidium iodide.

Figure 4:
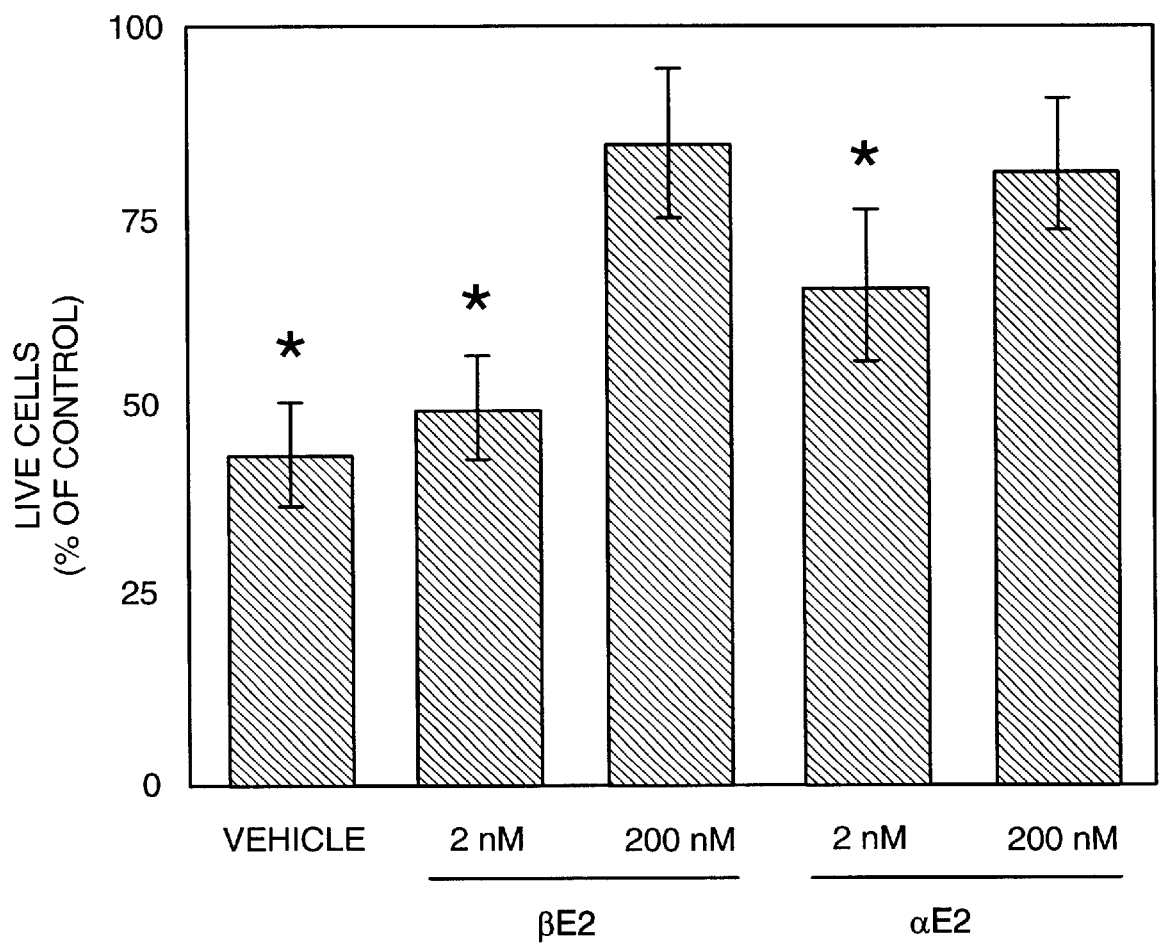
FIG. 4 shows the toxic effect of hypoglycemia and hypoxic conditions on the viability of cardiac myocytes and the cytoprotective effects of 17β-estradiol and 17α-estradiol. At concentrations of 200 nanomolar, both compounds had a significant protective effect on cardiac cells.

Exposure of H9c2 cells to hypoxic conditions in the absence of glucose resulted in approximately a 60% reduction in live cell number (FIG. 4). Both 17β-estradiol (βE2) and 17α-estradiol (αE2) robustly protected the cardiac cells from death as shown here, attenuating the toxic effects of glucose-free/hypoxic conditions. Treatment with 17β-estradiol caused a concentration-dependent increase in cell survival with approximately 85% of the cells surviving at the 200 nM dose. The cytoprotective effect of 17α-estradiol was equally strong, resulting in about 85% cell survival (FIG. 4). The asterisk indicates that the p value is less than 0.05, i.e., the data are statistically significant. Data are presented as the mean±SEM for 3 wells per group.

In a separate experiment, glucose deprivation under normal atmospheric conditions (10% $CO_2$/90% air) was determined to kill 32–57% of the H9c2 cells. This reduction in live cell number was almost completely blocked by concurrent treatment with 200 nM of either polycyclic phenolic compound, 17β-estradiol or 17α-estradiol. These compounds blocked 74% and 67% of this cell death, respectively. Hypoxia in the presence of glucose did not alter cell viability.

The increase in live cell number as a percentage of control appears to be through a cytoprotective mechanism rather than a mitogenic effect since neither steroid tested increased cell number in the absence of the toxicity. This example, in summary, illustrates that polycyclic phenolic compounds exert a cytoprotective effect on cardiac cells.

Example 5

In vitro Demonstration of the Cytoprotective Effect of Polycyclic Phenolic Compounds on Brain Capillary Endothelial Cells This example demonstrates the beneficial effect of utilizing polycyclic phenolic compounds for the protection of brain capillary endothelial cells. The in vitro assay is representative of a number of degenerative conditions, such as events that follow cerebral ischemia induced by occlusion of the middle cerebral artery (MCA) where oxygen and glucose supplies to the blood brain barrier endothelial cells are reduced.

Primary rat brain capillary endothelial cells (BCEC) cultures were prepared according to the method of Goldstein ((1975) J Neurochemistry 25: 715–717), incorporated herein by reference. The glucose concentration of the culture media was adjusted from 20 mg % to 200 mg % in separate culture dishes by adding appropriate amount of D-(+)-glucose to the glucose-free media. Glucose concentration was monitored by Glucose and L-Lactate Analyzer (YSI Model 2300 STAT Plus, YSI, Inc., Yellow Springs, Ohio). Following 24 hours of incubation with cell preparations, trypan blue staining was used to distinguish live cells from dead cells. Two cell countings at two different hemacytometer squares were averaged. The two-way analysis of variance was applied to determine the significance of the difference among the experimental groups. Kruskal-Wallis nonparametric analysis was used for data presented as percentage. The Mann-Whitney U tests were used when Kruskal-Wallis showed significance among groups. The mean±SEM are depicted (n=8–12). The asterisk indicates that the p value is less than 0.05, i.e., the data are statistically significant.

Figure 5:
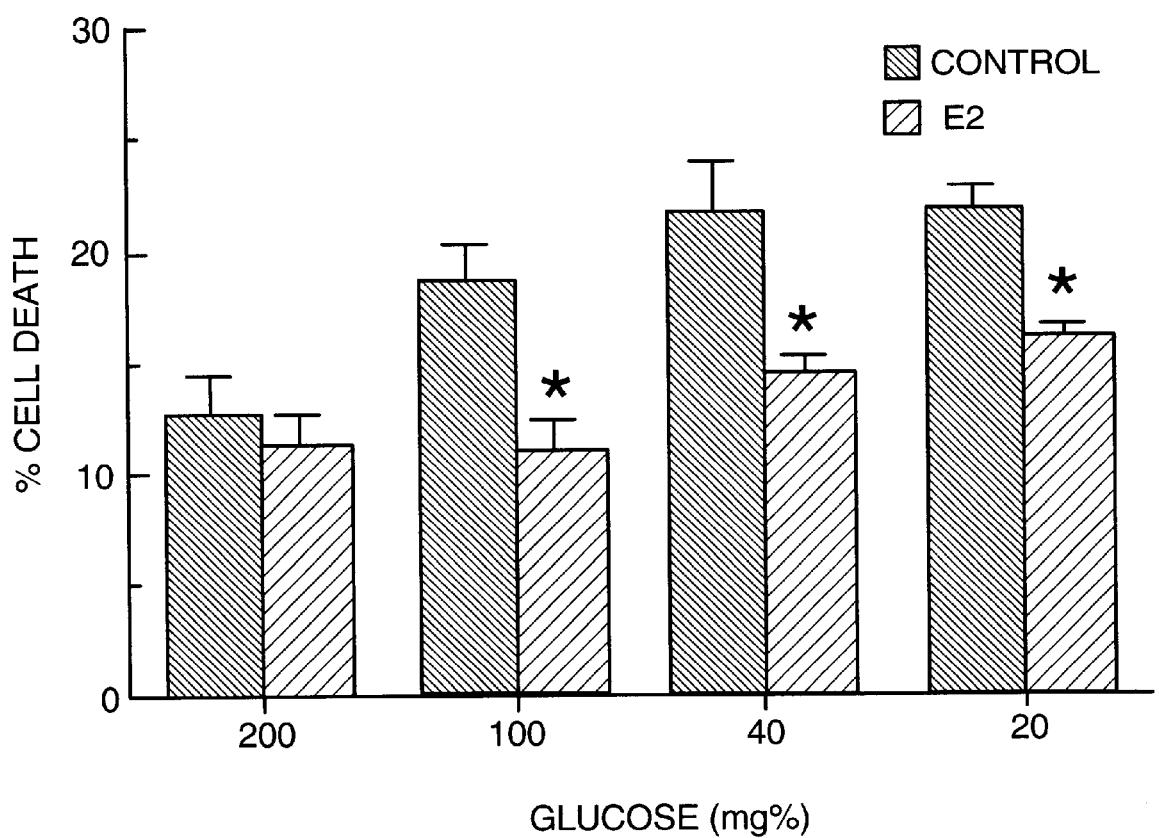
FIG. 5 shows the toxic effect of hypoglycemia on brain capillary endothelial cell cultures and the protective effects of 17β-estradiol. Maximal cell damage was obtained at 20, 40 or 100 mg % of glucose. In each example, 17β-estradiol had a significant cytoprotective effect on the endothelial cultures.

The normal glucose concentration in the cell culture medium is 200 mg %. As expected, there is essentially no augmentation in cell numbers in BCEC cultures when 17β-estradiol (E2) is added to the culture medium in 200 mg % glucose conditions (FIG. 5). Reduction in cell culture glucose levels to 100 mg %, 40 mg %, or 20 mg %, however, caused extensive cell death following 24 hours of hypoglycemia. In each case, cell survival was significantly enhanced by incubating hypoglycemic cultures in the presence of 17β-estradiol compared with corresponding control groups (FIG. 5). (The control groups consisted of parallel hypoglycemic cultures with the ethanol vehicle only). A similar beneficial effect was observed following a 48 hour hypoglycemic treatment.

Example 6

Comparison of the Cytoprotection Afforded by Various Different Four-ring Structures The studies described in Example 6 collectively show that a terminal phenolic structure is critical for effective cytoprotection. Certain compounds were tested that did not contain a terminal phenolic structure and in each case, these were determined to have little or no cytoprotection activity.

In each of the experiments of FIGS. 6, 7, 8 9 and 14, SK-N-SH cells were subjected to serum deprivation according to the procedure described in Bishop and Simpkins (1994) Mol Cell Neurosci 5: 303–308. In all studies, cells were cultured in RPMI-1640 media, RPMI-1640 media supplemented with 10% FBS or RPMI-1640 media supplemented one of the test compounds at a concentration of 2 nM. After incubation for 48 hours, surviving cells were assessed by trypan blue exclusion where live cells were those which excluded the dye and dead cells took up the trypan blue. All steroids were obtained from Steraloids, Inc., Newport, R.I. Compounds were initially dissolved at 1 mg/ml in absolute ethanol and diluted in RPMI-1640 media to a final concentration of 2 nM. To control for possible ethanol effects in the treated wells, both the serum-free media and FBS media were supplemented with absolute ethanol at a concentration of 544 pg/ml. In all studies, at least 4 and usually 6 replicate well were treated with each media.

Figure 6:
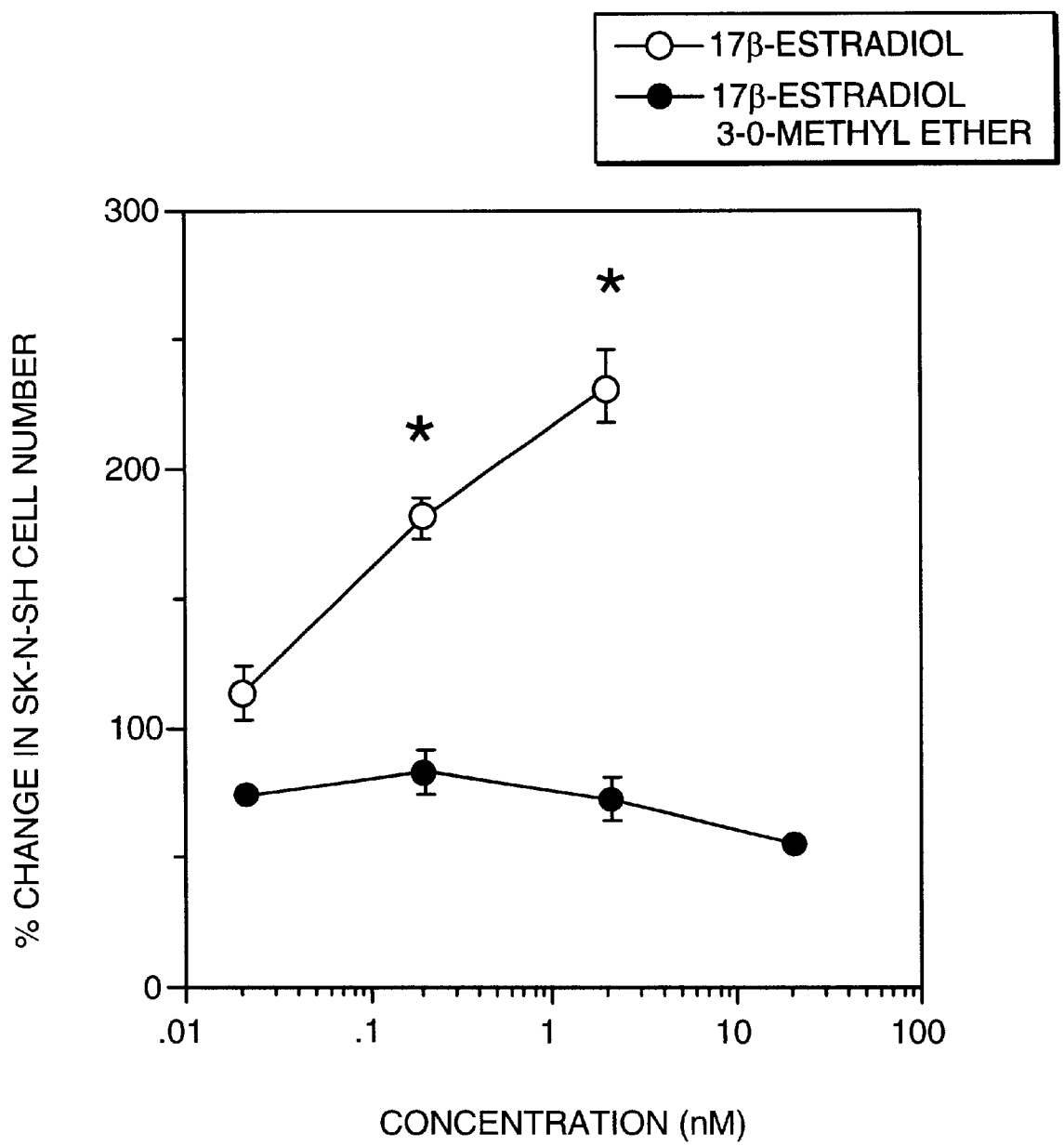
FIG. 6 shows the different effects of 17β-estradiol, a polycyclic phenolic compound, and 17β-estradiol 3-O-methyl ether, a compound that is not a polycyclic phenolic compound, on the percentage survival of SK-N-SH cells following serum deprivation. 17β-estradiol provided protection in a dose-dependent manner whereas no cytoprotection was noted with the nonpolycyclic phenolic compound.

FIG. 6 shows the dose-dependent effect of 17β-estradiol and 17β-estradiol-3-O-methyl ether on cell survival in the SK-N-SH serum deprivation model. As can be noted, 17β-estradiol is highly cytoprotective in a dose-dependent manner. In contrast, 17β-estradiol-3-O-methyl ether exhibits no protective effect at the lowest dose tested and the three higher doses tested similarly failed to protect cells from death. The latter compound has a substituent methyl group on the #3 position (see diagram of FIG. 13(A)), which leads to an abolishment of cell protection activity.

Figure 7:
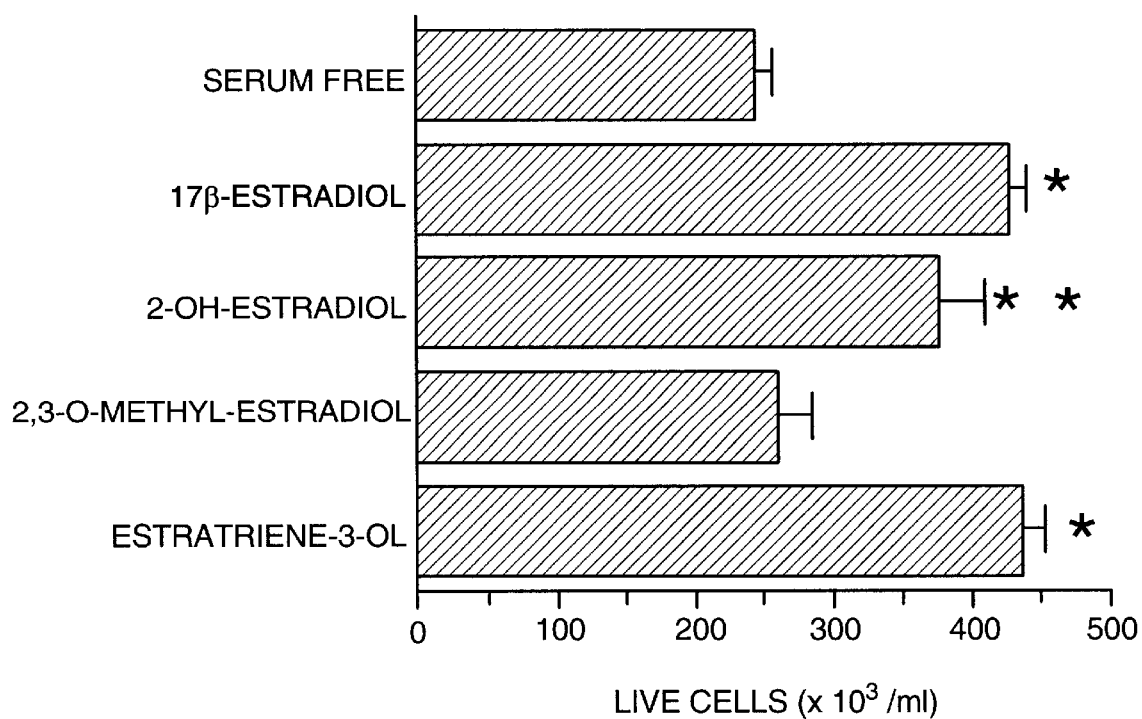
FIG. 7 shows the cytoprotective effects of 17β-estradiol, 2-OH-estradiol, 2,3-O-methyl estradiol and estratriene-3-ol on SK-N-SH cells following serum deprivation. The polycyclic phenolic compounds, 17β-estradiol, 2-OH-estradiol and estratriene-3-ol, were highly protective in contrast to 2,3-O-methyl estradiol.

FIG. 7 compares the effect of 17β-estradiol, 2-OH-estradiol, 2,3-O-methyl estradiol and estratriene-3-ol on cell survival in the SK-N-SH serum deprivation model. Compounds with terminal phenolic rings, namely, 17β-estradiol, 2-OH-estradiol and estratriene-3-ol were all highly neuroprotective, whereas 2,3-O-methyl estradiol, a compound without a terminal phenolic group, failed to show cell protection. The latter compound was equivalent to serum-free conditions.

FIG. 8 compares the effect of estriol, a compound with a terminal phenolic ring and estriol-3-O-ME, a compound lacking the terminal phenolic ring due to a methyl group added to the #3 position. The latter compound is not cytoprotective. The figure also compares ethynyl estradiol to ethynyl estradiol-3-O-ME. Again, the latter compound is not cytoprotective and lacks a terminal phenolic ring due to a methyl group added to the #3 position.

FIG. 14 compares the effect of pairs of molecules, one a polycyclic phenolic compound and the other a compound without a terminal phenolic group on cell survival in the SK-N-SH serum deprivation model. In each case, addition of a methyl group to the #3 position (or in the case of 2,3-O-methyl estradiol in the #2 and #3 positions) leads to abolishment of cytoprotection activity compared to the analogous compound with a substituent hydroxyl moiety.

Example 7

Figure 10A:
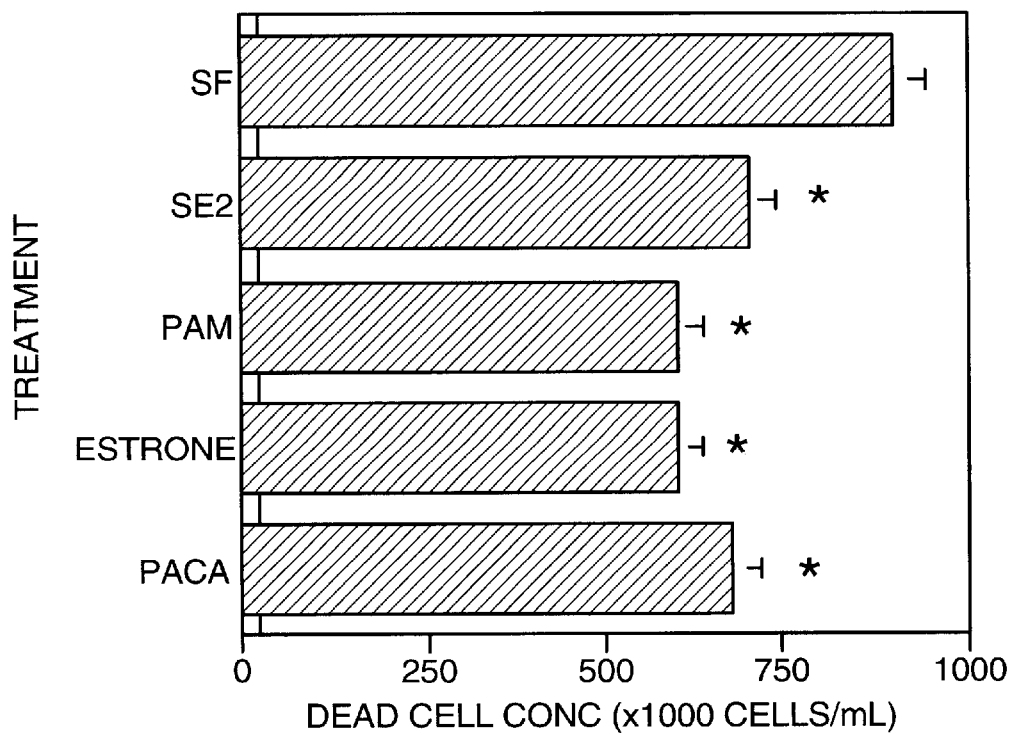
FIG. 10 (A) and (B) show the cytoprotective effects of 17β-estradiol, estrone, [2S-(2a,4aα, 10aβ]-1,2,3,4,4a,9,10,10a-octahydro-7-hydroxy-2-methyl-2-phenanthrenemethanol (PAM) and [2S-(2a,4aα, 10aβ]-1,2,3,4,4a,9,10,10a-octahydro-7-hydroxy-2-methyl-2-phenanthrenecarboxyaldehyde (PACA) on SK-N-SH cells following serum deprivation.
Figure 10B:
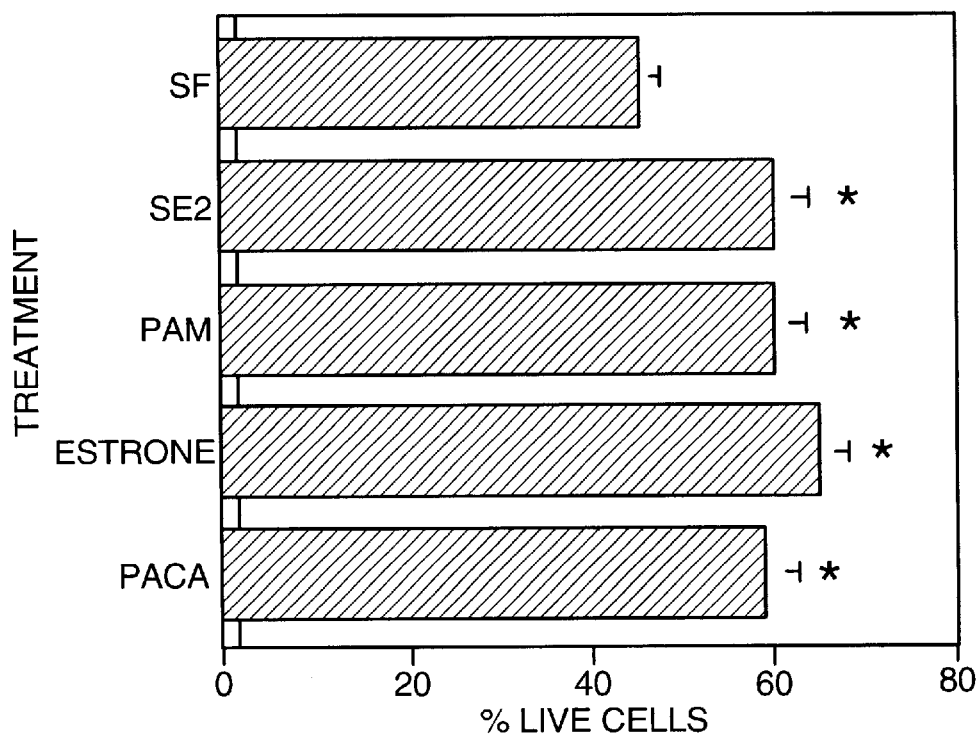
Figure 11A:
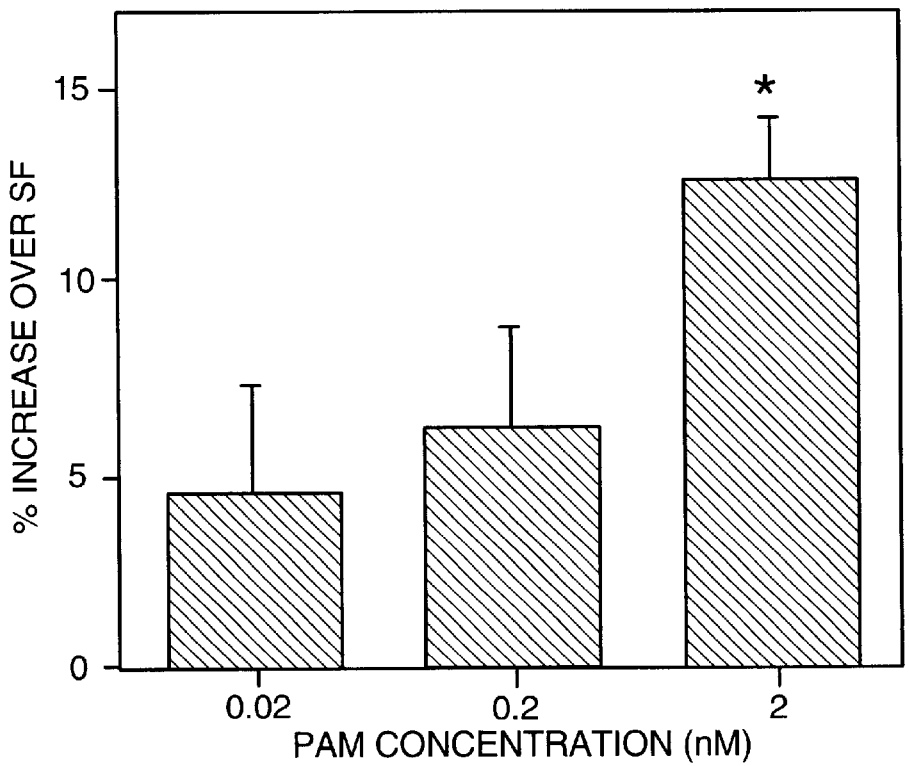
FIG. 11 (A) and (B) show the dose-dependent cytoprotective effects of [2S-(2a,4aα,10aβ]-1,2,3,4,4a,9,10,10a-octahydro-7-hydroxy-2-methyl-2-phenanthrenemethanol (PAM) and [2S-(2a,4aα, 10aβ]-1,2,3,4,4a,9,10,10a-octahydro-7-hydroxy-2-methyl-2-phenanthrenecarboxyaldehyde (PACA) on SK-N-SH cells following serum deprivation.
Figure 11B:
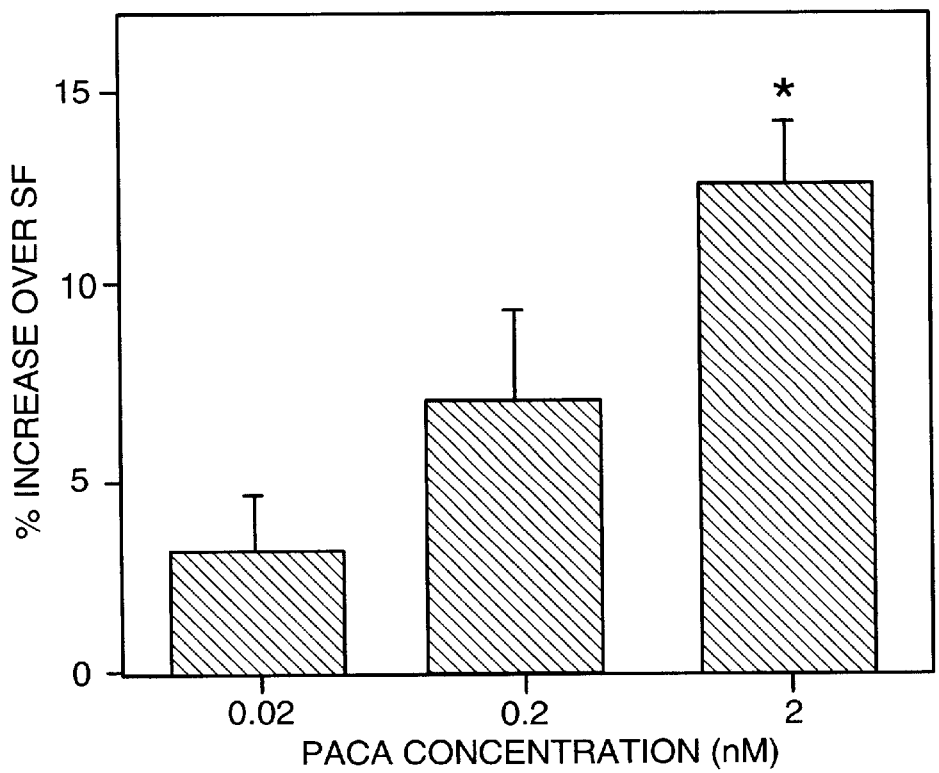
Figure 12:
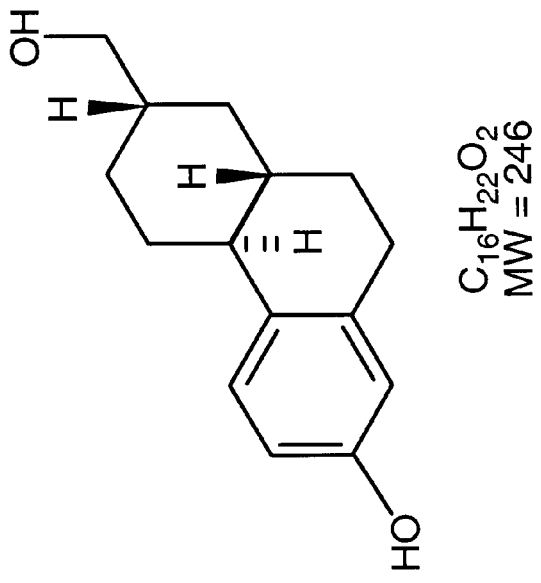
FIG. 12 shows the structures of 3-ring compounds: [2S-(2a,4aα,10aβ)]-1,2,3,4,4a,9,10,10a-octahydro-7-hydroxy-2-methyl-2-phenanthrenemethanol (PAM) and [2S-(2a,4aα, 10aβ)]-1,2,3,4,4a,9,10,10a-octahydro-7-hydroxy-2-methyl-2-phenanthrenecarboxaldehyde (PACA).
Figure 12:
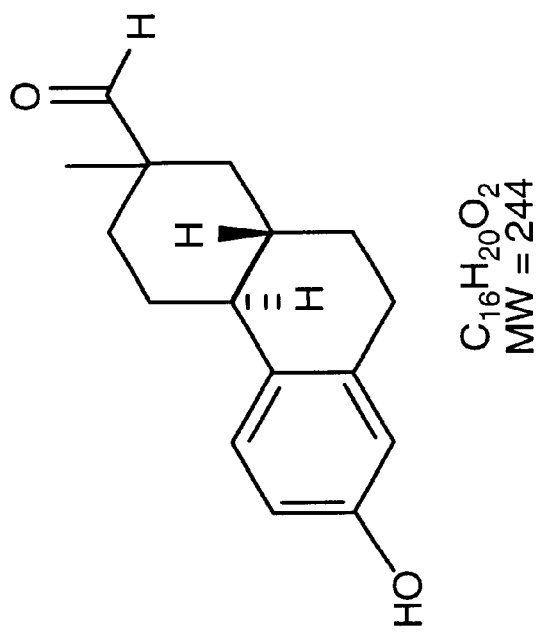
Figure 13A:
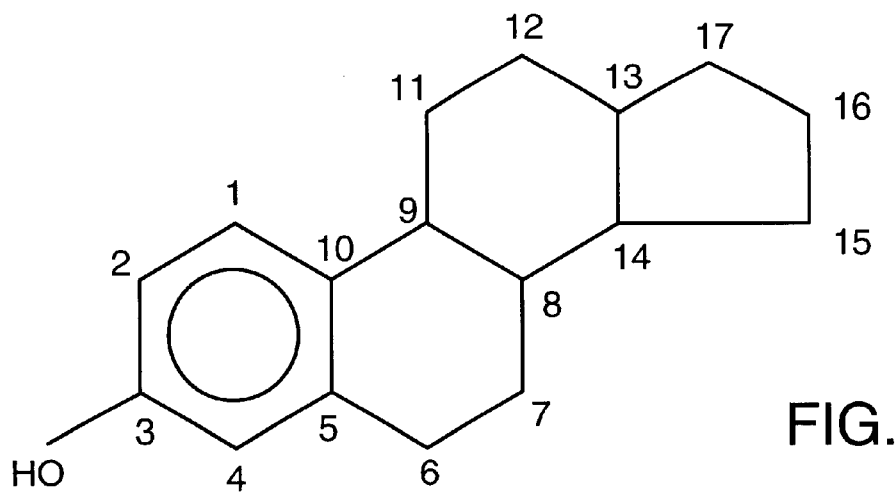
FIGS. 13A–D show the generalized core ring structures with numbered carbons; (A) 4-ring structure, (B) 3-ring structure, (C) 2-ring structure (fused), (D) 2-ring structure (non-fused).
Figure 13B:
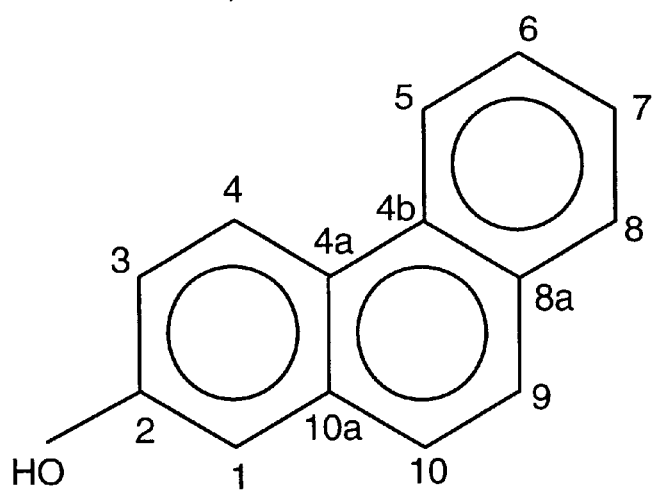
Figure 13C:
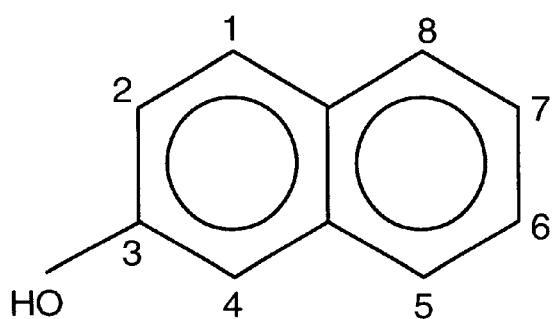
Figure 13D:
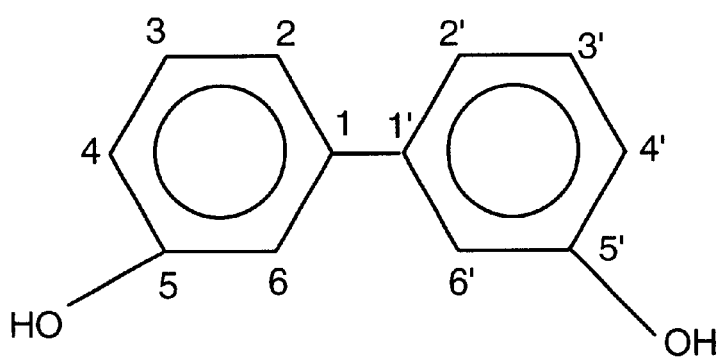

Comparison of the Cytoprotection Afforded by Various Different Two-ring and Three-ring Structures FIGS. 10 and 11 show the cell protective effects of two three-ring compounds: [2S-(2a, 4aα, 10αβ)]-1,2,3,4,4a,9,10,10a-octaydro-7hydroxy-2-methyl-2-phenanthrenemethanol (PAM) and [2S-(2a,4aα,10αβ)]-1,2,3,4,4a,9,10,10a-octaydro-7hydroxy-2-methyl-2-phenanthrenecarboxyaldehyde (PACA). Structures of these compounds is shown in FIG. 12. Compounds were added to SK-N-SH cell cultures subjected to serum deprivation and cell viability was assessed as described in Example 6. Both PAM and PACA showed neuroprotective activity with peak responses at the 2 nM concentration (FIG. 11). Neuroprotective activity was similar to the positive control, 17βestradiol (FIG. 10).

The two-ring non-fused diethylstilbestrol (DES), was active as a neuroprotectant and retained nearly full neuroprotectivity when one, but not both, of the phenolic hydroxyl functions were replaced with an O-methyl ether function (FIGS. 9 and 15). Similarly, all steroids were rendered inactive when the 3-hydroxyl group was replaced with an O-methyl ether group (FIG. 6, 7, 8 and 14). The 3-O methyl ether of 17β-estradiol was inactive even at concentrations as high as 20 nM (FIG. 6). The data of Example 6 provides further confirmation that C-3 hydroxylated estratrienes with terminal phenolic groups are neuroprotective. A similarly positioned phenolic hydroxyl group in the di- and triphenols may serve the same function as in the four-ring structures.

Example 8

Comparison of the Cytoprotection Afforded by Additional Steroid Structures

Six additional steroids were evaluated at 2 nM concentrations for neuroprotection in the SK-N-SH nutrient deprivation cell protection assay. The following results expressed as per ml quantities were obtained for live cells/ml (mean+ SEM×$10^3$/ml) for 5 to 6 cultures/group. Study 1: serum free controls=94±7; testosterone=87±6; dihydrotestosterone= 90±7; cholesterol=65±4. Study 2: serum free controls= 177±18; 17β-estradiol=329±33 (p<0.05 vs serum free controls); prednisolone=187±16; 6α-methylprednisolone= 173±13; aldosterone=132±18. No neuroprotective effect was observed for any non-phenolic steroids.

The two androgens containing a C-3 ketone but which lack terminal phenolic rings, namely the partially unsaturated testosterone and the saturated compound, dihydrotestosterone, were both inactive. Similarly, progesterone and aldosterone and two $\Delta^{1,4}$-steroids, prednisolone and 6-methylprednisolone, were not cytoprotective. Finally, cholesterol was tested because it has a 3-hydroxyl function but on a completely saturated A ring. The compound failed to confer cell protection.

We claim:

1. A method for conferring a cytoprotective effect on a population of cells, comprising:
    (a) providing a polycyclic phenolic compound in a physiologically acceptable formulation wherein the phenol in the compound is located at a terminal position such that the compound with the terminal phenol has a substantially enhanced cytoprotective effect in a cell based assay compared with the compound lacking the terminal phenol; and
    (b) administering the formulation in an effective dose to the population of cells to confer cytoprotection.

2. A method according to claim 1, wherein the polycyclic phenolic compound has a molecular weight of less than 1000 Daltons.

3. A method according to claim 1, wherein the polycyclic phenolic compound has a molecular weight of greater than 170 Daltons.

4. A method according to claim 2, wherein the compound comprises a four-ring structure.

5. A method for conferring cytoprotection in a population of cells in a subject, comprising:
    (a) providing a polycyclic phenolic compound in a physiologically acceptable formulation wherein the phenol in the compound is located at a terminal position such that the compound with the terminal phenol has a substantially enhanced cytoprotective effect in a cell based assay compared with the compound lacking the terminal phenol; and
    (b) administering the formulation in an effective dose to the subject to confer cytoprotection.

6. A method according to claim 5, wherein the polycyclic phenolic compound has a molecular weight of less than 1000 Daltons.

7. A method according to claim 6, wherein the polycyclic phenolic compound has a molecular weight of greater than 170 Daltons.

8. A method according to claim 5, wherein the compound comprises a four-ring structure.

9. A method according to claim 5, wherein the effective dose provides a tissue concentration of the compound that is equal to or less than 200 nM.

10. A method according to claim 1 or 5, further comprising: administering an additional one or more compound, wherein the additional compound comprises a polycyclic phenolic compound.

11. A method according to claim 5, wherein the step of administering the compound in a subject further comprises: administering the compound by a delivery route selected from oral, intramuscular, transdermal, nasal, buccal, intravenous, rectal and subcutaneous delivery routes.

12. A method according to claim 5, wherein the step of administering the compound in a subject further comprises administering the compound in a unit dose or utilizing a controlled release vehicle.

13. A method according to claim 5, wherein the population of cells is selected from stem cells, blood cells, cells of the central nervous system, cells of the peripheral nervous system, connective tissue cells, muscle tissue cells, endocrine tissue cells, whole organ cells, bone cells, eye cells, reproductive tract cells and urinary tract cells.

14. A method according to claim 5, wherein cytoprotection slows the progression of a disease, wherein the disease is a degenerative disease.

15. A method according to claim 14, wherein the disease is a bone disorder.

16. A method according to claim 15, wherein the bone disorder is selected from osteoporosis, osteomyelitis, ischemic bone disease, fibrous dysplasia, rickets, Cushing's syndrome and osteoarthritis.

17. A method according to claim 14, wherein the disease is a cardiac disorder.

18. A method according to claim 17, wherein the cardiac disorder is selected from cardiac ischemia, myocardial infarction, chronic or acute heart failure, cardiac dysrhymias, atrial fibrillation, paroxymial tachycardia, ventricular fibrillation and congestive heart failure.

19. A method according to claim 14, wherein the disease is an eye disorder.

20. A method according to claim 19, wherein the eye disorder is selected from macular degeneration and retinal degeneration.

21. A method according to claim 14, wherein the disease is selected from a skin disorder, a pulmonary disorder, a hepatic disorder, a renal disorder, a vascular disorder and an autoimmune disorder.

22. A method for conferring a cytoprotective effect on a population of cells, comprising:
    (a) providing a polycyclic compound having a terminal phenolic ring, any of one, two or three additional ring structures, and a molecular weight in the range of 170–1000 daltons, in a physiologically acceptable formulation; and
    (b) administering the formulation in an effective dose to the population of cells to confer cytoprotection.

23. A method according to claim 22, wherein the compound has 3 additional carbon rings linked to the terminal phenolic ring.

24. A method according to claim 22, wherein the cell population is in a subject.

25. A method according to claim 22 or 24 further comprising: administering an additional one or more compound, wherein the additional compound comprises a polycyclic phenolic compound.

26. A method according to claim 24, wherein the step of administering the compound in a subject includes utilizing any administration route selected from oral, intramuscular, transdermal, nasal, buccal, intravenous, rectal and subcutaneous.

27. A method according to claim 24, wherein the step of administering the compound in a subject further comprises administering a unit dose or utilizing a controlled release vehicle.

28. A method according to claim 22 or 24, wherein the population of cells is selected from stem cells, blood cells, connective tissue cells, muscle tissue cells, endocrine tissue cells, whole organ cells, bone cells, eye cells, reproductive tract cells and urinary tract cells.

29. A method according to claim 24, wherein cytoprotection slows the progression of a disease, wherein the disease is a degenerative disease.

30. A method according to claim 29, wherein the disease is a bone disorder.

31. A method according to claim 30, wherein the bone disorder is selected from osteoporosis, osteomyelitis, ischemic bone disease, fibrous dysplasia, rickets, Cushing's syndrome and osteoarthritis.

32. A method according to claim 29, wherein the disease is an eye disorder.

33. A method according to claim 32, wherein the eye disorder is selected from macular degeneration and retinal degeneration.

34. A method according to claim 29, wherein the disease is a cardiac disorder.

35. A method according to claim 34, wherein the cardiac disorder is selected from cardiac ischemia, myocardial infarction, chronic or acute heart failure, cardiac dysrhymias, atrial fibrillation, paroxymial tachycardia, ventricular fibrillation and congestive heart failure.

36. A method according to claim 29, wherein the disease is selected from a skin disorder, a pulmonary disorder, a hepatic disorder, a renal disorder, a vascular disorder and an autoimmune disorder.

* * * * *